(12) United States Patent
Walden et al.

(10) Patent No.: US 8,814,804 B2
(45) Date of Patent: Aug. 26, 2014

(54) INTERACTIVE BLOOD-ALCOHOL CONTENT TESTER

(75) Inventors: Eugene D. Walden, Eden Prairie, MN (US); Whitney B. Walden, Eden Prairie, MN (US); Ryan B. Walden, Eden Prairie, MN (US)

(73) Assignee: IPH, LLC, Lewiston, MN (US)

( * ) Notice: Subject to any disclaimer, the term of this patent is extended or adjusted under 35 U.S.C. 154(b) by 314 days.

(21) Appl. No.: 13/324,600

(22) Filed: Dec. 13, 2011

(65) Prior Publication Data

US 2012/0157871 A1    Jun. 21, 2012

Related U.S. Application Data

(60) Provisional application No. 61/459,449, filed on Dec. 13, 2010, provisional application No. 61/569,616, filed on Dec. 12, 2011.

(51) Int. Cl.
*A61B 5/08*    (2006.01)
(52) U.S. Cl.
USPC .......................................... 600/532; 600/543
(58) Field of Classification Search
USPC .......................................... 600/532, 538, 543
See application file for complete search history.

(56) References Cited

U.S. PATENT DOCUMENTS

| | | | |
|---|---|---|---|
| 3,877,291 A | | 4/1975 | Hoppesch et al. |
| 4,140,106 A | * | 2/1979 | Kirmaier ....................... 600/532 |
| 4,248,245 A | * | 2/1981 | Kempin ........................ 600/532 |
| 4,297,871 A | * | 11/1981 | Wright et al. .................. 73/23.3 |
| 4,314,564 A | * | 2/1982 | Albarda ......................... 600/532 |
| 4,316,380 A | * | 2/1982 | Heim et al. .................... 73/23.3 |
| 4,487,055 A | * | 12/1984 | Wolf .............................. 73/23.3 |
| 4,607,719 A | * | 8/1986 | Rugis et al. .................. 180/272 |
| 4,649,027 A | * | 3/1987 | Talbot ............................ 422/84 |

(Continued)

FOREIGN PATENT DOCUMENTS

| | | |
|---|---|---|
| EP | 0 302 681 A2 | 2/1989 |
| GB | 2 201 245 A | 8/1988 |

(Continued)

OTHER PUBLICATIONS

Lifeloc Technologies, "New Educational IPhone App from Lifeloc Technologies", Mar. 10, 2011, 1 page.

(Continued)

*Primary Examiner* — Jacqueline Cheng
*Assistant Examiner* — Corey B Hipps
(74) *Attorney, Agent, or Firm* — Patterson Thuente Pedersen, P.A.

(57) ABSTRACT

A blood-alcohol content (BAC) tester for use at a facility serving alcohol. The BAC tester includes a breath-sampling unit having an air-chamber unit defining a closed position and an open position. The air-chamber unit has a first air-chamber block and a second air-chamber block, the first air-chamber block and the second air-chamber block defining an air chamber for receiving air exhaled from a user. The breath-sampling unit also includes a drive unit coupled to the second air-chamber block and an alcohol sensor. The BAC tester also includes a sensor circuit communicatively coupled to the drive unit and the alcohol sensor. The sensor circuit is configured to cause the drive unit to move the second-air chamber block relative to the first air-chamber block so as to cause the air-chamber unit to be in the closed or the open position.

5 Claims, 15 Drawing Sheets

(56) References Cited

U.S. PATENT DOCUMENTS

| | | | |
|---|---|---|---|
| 4,736,619 A | 4/1988 | Legrand | |
| 4,749,553 A | 6/1988 | Lopez et al. | |
| 4,770,026 A | 9/1988 | Wolf | |
| 4,809,810 A * | 3/1989 | Elfman et al. | 180/272 |
| 4,821,737 A * | 4/1989 | Nelson | 600/543 |
| 4,914,720 A * | 4/1990 | Knodle et al. | 250/343 |
| 5,055,268 A | 10/1991 | Martin | |
| 5,291,898 A * | 3/1994 | Wolf | 600/532 |
| 5,303,575 A | 4/1994 | Brown et al. | |
| 5,515,859 A | 5/1996 | Paz | |
| 5,540,222 A * | 7/1996 | Younes | 128/205.18 |
| 5,739,412 A * | 4/1998 | Stock et al. | 73/23.3 |
| 5,868,681 A * | 2/1999 | Schiller | 600/533 |
| 5,929,319 A | 7/1999 | King et al. | |
| 5,971,937 A * | 10/1999 | Ekstrom | 600/532 |
| 6,177,051 B1 | 1/2001 | Kimelman | |
| 6,205,840 B1 * | 3/2001 | Thompson | 73/23.3 |
| 6,244,096 B1 * | 6/2001 | Lewis et al. | 73/23.2 |
| 6,319,724 B1 * | 11/2001 | Lewis et al. | 436/149 |
| 6,464,941 B1 * | 10/2002 | Diekmann | 422/84 |
| 6,467,333 B2 * | 10/2002 | Lewis et al. | 73/31.05 |
| 6,620,107 B2 * | 9/2003 | Payne et al. | 600/532 |
| 6,726,636 B2 * | 4/2004 | Der Ghazarian et al. | 600/532 |
| 6,748,792 B1 * | 6/2004 | Freund et al. | 73/23.3 |
| 6,792,793 B2 * | 9/2004 | Mendoza | 73/23.3 |
| 6,837,095 B2 | 1/2005 | Sunshine et al. | |
| 6,841,391 B2 * | 1/2005 | Lewis et al. | 436/149 |
| 6,858,182 B1 * | 2/2005 | Ito et al. | 422/416 |
| 6,923,040 B2 * | 8/2005 | Stock | 73/23.3 |
| 7,171,842 B2 * | 2/2007 | Stock et al. | 73/23.3 |
| 7,287,687 B2 | 10/2007 | Vercnocke et al. | |
| 7,329,390 B2 * | 2/2008 | Stock et al. | 422/84 |
| 7,341,693 B2 | 3/2008 | Der Ghazarian et al. | |
| 7,462,149 B2 | 12/2008 | Hawthorne et al. | |
| 7,603,886 B2 * | 10/2009 | Stock | 73/23.3 |
| 7,603,887 B2 * | 10/2009 | Schlichte | 73/23.3 |
| 7,797,982 B2 | 9/2010 | Burke et al. | |
| 7,833,166 B2 * | 11/2010 | Ruffert | 600/532 |
| 7,841,224 B2 * | 11/2010 | Son | 73/1.02 |
| 7,914,460 B2 * | 3/2011 | Melker et al. | 600/532 |
| 7,919,754 B2 * | 4/2011 | Hok et al. | 250/339.13 |
| 7,993,281 B2 * | 8/2011 | Stock et al. | 600/532 |
| 8,183,527 B2 * | 5/2012 | Taguchi et al. | 250/339.13 |
| 8,240,419 B2 * | 8/2012 | Zimmermann et al. | 180/272 |
| 8,250,900 B2 * | 8/2012 | Son | 73/1.02 |
| 8,359,901 B2 * | 1/2013 | Freund et al. | 73/23.3 |
| 8,418,796 B2 * | 4/2013 | Flores | 180/272 |
| 8,590,363 B2 * | 11/2013 | Burke et al. | 73/23.3 |
| 8,613,707 B2 * | 12/2013 | Peyton | 600/504 |
| 8,657,757 B2 * | 2/2014 | Lazar et al. | 600/538 |
| 2001/0041366 A1 * | 11/2001 | Lewis et al. | 436/151 |
| 2002/0017125 A1 * | 2/2002 | Lewis et al. | 73/31.05 |
| 2002/0084130 A1 | 7/2002 | Der Ghazarian et al. | |
| 2002/0127145 A1 * | 9/2002 | Der Ghazarian et al. | 422/83 |
| 2002/0131898 A1 * | 9/2002 | Fleischer et al. | 422/82.01 |
| 2003/0023182 A1 * | 1/2003 | Mault et al. | 600/532 |
| 2003/0117287 A1 | 6/2003 | Crespo | |
| 2003/0176803 A1 * | 9/2003 | Gollar | 600/532 |
| 2003/0228702 A1 * | 12/2003 | Stock et al. | 436/133 |
| 2004/0138823 A1 * | 7/2004 | Gollar | 702/19 |
| 2004/0147038 A1 * | 7/2004 | Lewis et al. | 436/149 |
| 2004/0154377 A1 * | 8/2004 | Stock | 73/23.3 |
| 2004/0204655 A1 * | 10/2004 | Stock et al. | 600/532 |
| 2005/0053523 A1 * | 3/2005 | Brooke | 422/68.1 |
| 2006/0193749 A1 * | 8/2006 | Ghazarian et al. | 422/83 |
| 2006/0206034 A1 * | 9/2006 | Stock et al. | 600/532 |
| 2006/0282344 A1 | 12/2006 | Brown | |
| 2007/0016092 A1 * | 1/2007 | Shaw et al. | 600/532 |
| 2007/0093725 A1 * | 4/2007 | Shaw | 600/543 |
| 2007/0173731 A1 * | 7/2007 | Meka et al. | 600/543 |
| 2007/0193335 A1 * | 8/2007 | Son | 73/23.3 |
| 2007/0232950 A1 * | 10/2007 | West | 600/532 |
| 2007/0245801 A1 * | 10/2007 | Stock | 73/23.3 |
| 2007/0283745 A1 | 12/2007 | Pfeiffer | |
| 2008/0056946 A1 * | 3/2008 | Ahmad | 422/68.1 |
| 2008/0061238 A1 * | 3/2008 | Hok et al. | 250/340 |
| 2008/0078232 A1 * | 4/2008 | Burke et al. | 73/23.3 |
| 2008/0294059 A1 * | 11/2008 | Arias | 600/532 |
| 2008/0314115 A1 * | 12/2008 | Faulder et al. | 73/23.3 |
| 2009/0054799 A1 * | 2/2009 | Vrtis et al. | 600/532 |
| 2009/0087920 A1 * | 4/2009 | Pettersson et al. | 436/132 |
| 2009/0187111 A1 * | 7/2009 | Reilly et al. | 600/532 |
| 2010/0012417 A1 * | 1/2010 | Walter et al. | 180/272 |
| 2010/0025585 A1 * | 2/2010 | Taguchi et al. | 250/339.13 |
| 2010/0028210 A1 | 2/2010 | Ozaki et al. | |
| 2010/0063408 A1 * | 3/2010 | Nothacker et al. | 600/532 |
| 2010/0085067 A1 * | 4/2010 | Gabriel et al. | 324/663 |
| 2010/0089121 A1 * | 4/2010 | Hemmingsson et al. | 73/23.3 |
| 2010/0097380 A1 * | 4/2010 | Daniels et al. | 345/440.2 |
| 2010/0138166 A1 | 6/2010 | Do et al. | |
| 2010/0204600 A1 * | 8/2010 | Crucilla | 600/532 |
| 2010/0324439 A1 * | 12/2010 | Davenport | 600/532 |
| 2011/0001625 A1 * | 1/2011 | Reilly et al. | 340/632 |
| 2011/0009762 A1 * | 1/2011 | Eichler et al. | 600/532 |
| 2011/0009765 A1 * | 1/2011 | Gollar | 600/532 |
| 2011/0072884 A1 * | 3/2011 | Burke et al. | 73/23.3 |
| 2011/0079073 A1 | 4/2011 | Keays | |
| 2011/0088446 A1 * | 4/2011 | Son | 73/1.06 |
| 2011/0093283 A1 | 4/2011 | Dicks et al. | |
| 2011/0178420 A1 * | 7/2011 | Ridder et al. | 600/532 |
| 2011/0257973 A1 | 10/2011 | Chutorash et al. | |
| 2011/0263947 A1 | 10/2011 | Utley et al. | |
| 2011/0283770 A1 * | 11/2011 | Hok | 73/23.3 |
| 2012/0022890 A1 * | 1/2012 | Williams et al. | 705/3 |
| 2012/0031165 A1 * | 2/2012 | Ruocco et al. | 73/23.3 |
| 2012/0165694 A1 * | 6/2012 | Meka et al. | 600/532 |
| 2012/0212735 A1 * | 8/2012 | Palmskog et al. | 356/301 |
| 2012/0244371 A1 * | 9/2012 | Flores | 428/542.2 |
| 2012/0291517 A1 * | 11/2012 | Son | 73/1.06 |
| 2012/0302907 A1 * | 11/2012 | Palmskog et al. | 600/532 |
| 2012/0330175 A1 * | 12/2012 | Phillips et al. | 600/532 |
| 2013/0150746 A1 * | 6/2013 | Tao et al. | 600/531 |
| 2013/0208359 A1 * | 8/2013 | Matsuno et al. | 359/578 |
| 2013/0231871 A1 * | 9/2013 | Hok et al. | 702/19 |

FOREIGN PATENT DOCUMENTS

| | | |
|---|---|---|
| GB | 2 269 901 A | 2/1994 |
| GB | 2 295 234 A | 5/1996 |
| WO | WO 01/63277 A1 | 8/2001 |

OTHER PUBLICATIONS

Don Bassler et al., "Blow into the iBreath and your iPod plays a blood-alcohol alert", Ridecharge, https://www.ridecharge.com/en/news/article/21, Nov. 3, 2011, 5 pages.

Lifeloc Technologies, "Breath Alcohol Testing Kiosks", http://www.lifeloc.com/products/kiosk.html, Nov. 3, 2011, 2 pages.

LifeGuard Breath Tester, "Pesonal Breathalyzer: New Solution to DUI Problem", http://lifeguardbreathtester.com/drunkguard.shtml, Nov. 3, 2011, 2 pages.

Ladybug Teknologies, "The SipSmart Program", http://spismart.ca/the-sipsmart-program, Oct. 27, 2011, 6 pages.

AL4000 Wireless Credit Card, Alcomate, http://alcomate.net/index.php/alcoscan-a14000.html, Nov. 3, 2011, 2 pages.

AlcoTester.com, AlcoScan AL-3500 S/C Dollar Bill Operated Breathalyzer, http://www.alcotester.com/products/AlcoScan-AL%252d3500-S%7B47%DC-Dollar-Bill, Nov. 3, 2011, 4 pages.

Blo Dad & Sons, Boozelator™ 3001, http://boozelator3001.com, Nov. 3, 2011, 2 pages.

* cited by examiner

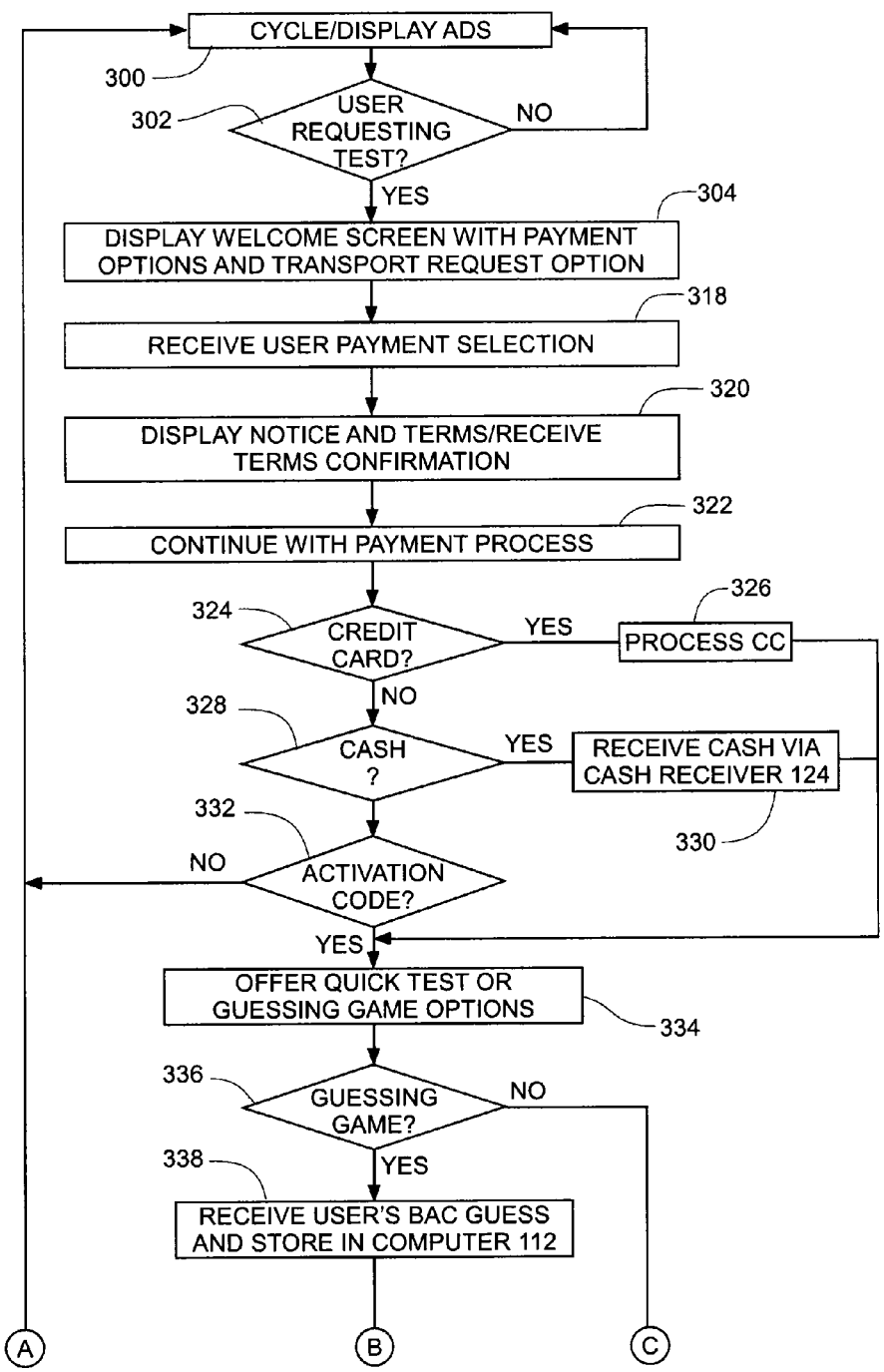

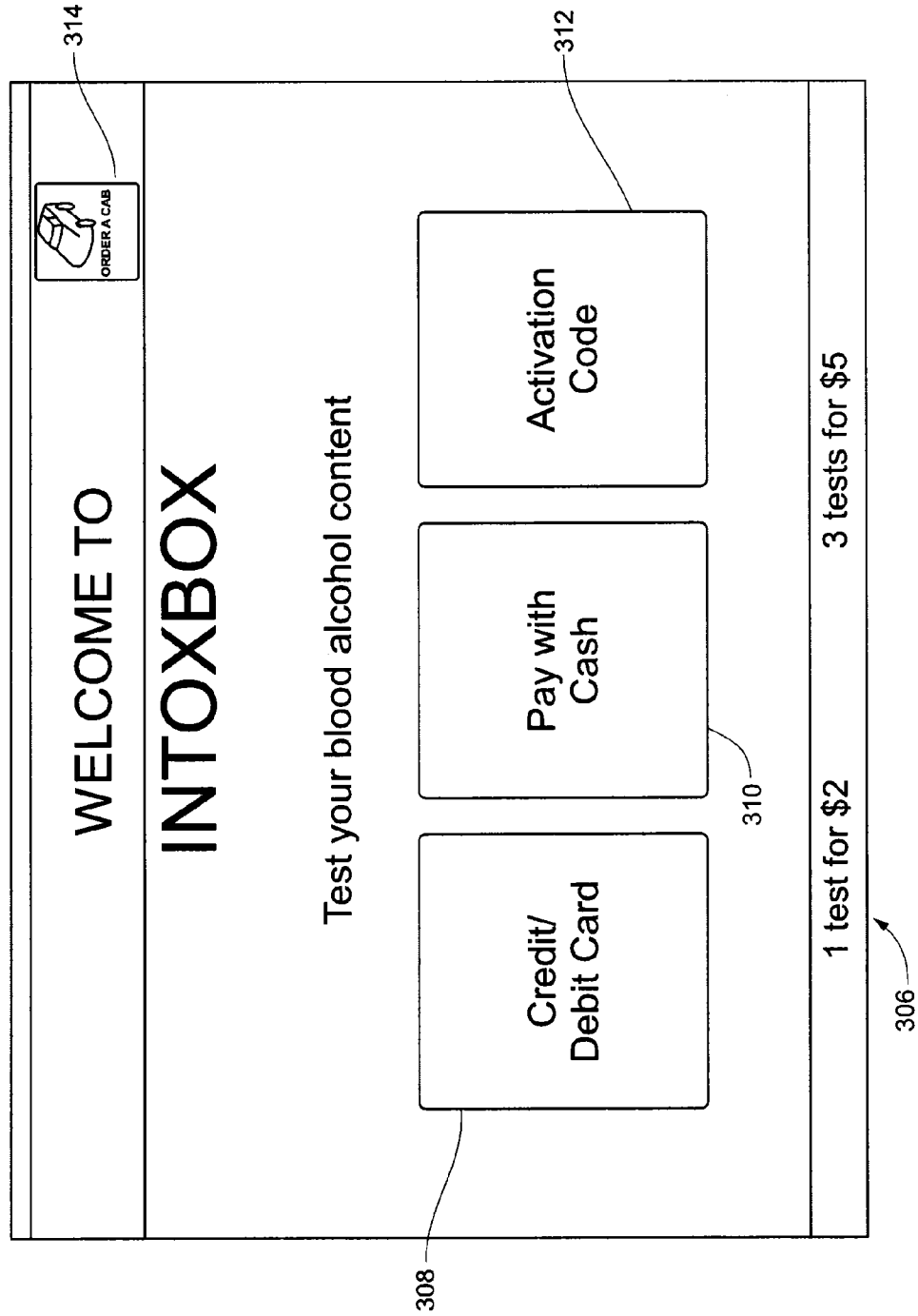

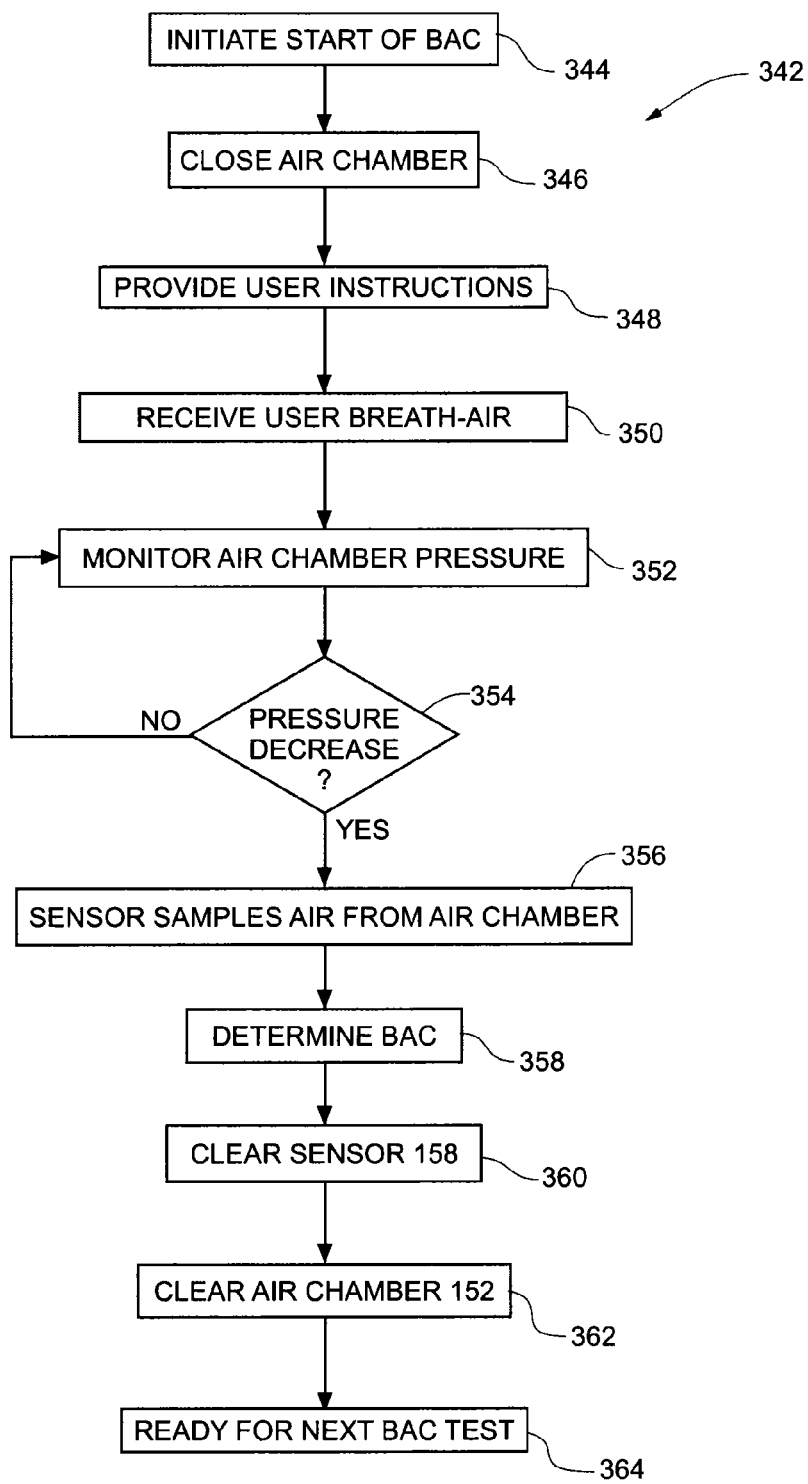

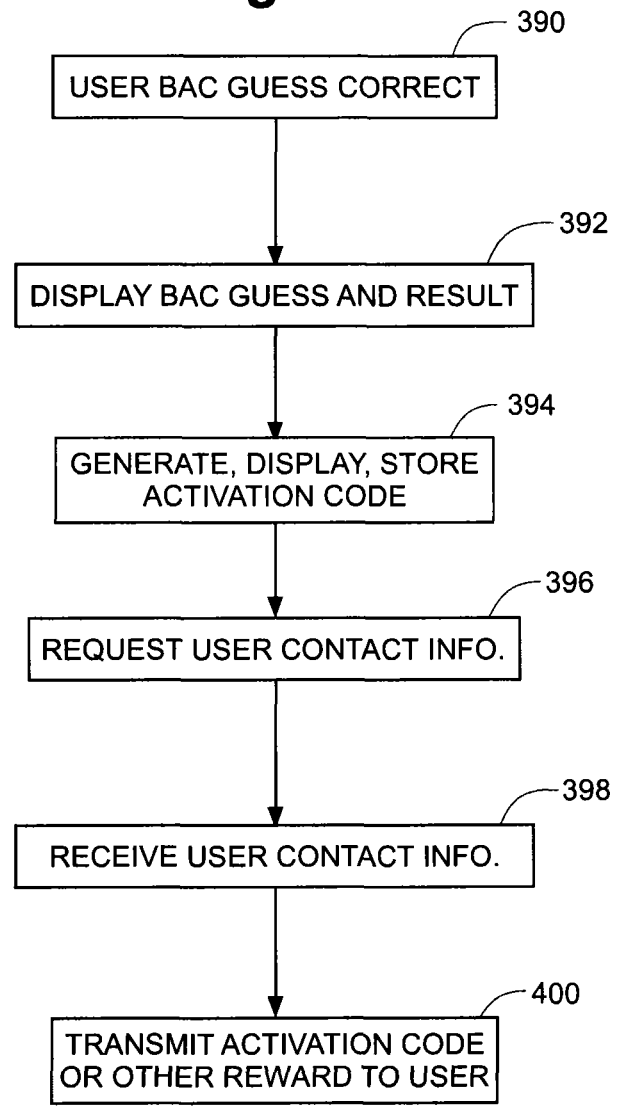

INTERACTIVE BLOOD-ALCOHOL CONTENT TESTER

RELATED APPLICATION

The present application claims the benefit of U.S. Provisional Application No. 61/459,449 filed Dec. 13, 2010, and U.S. Provisional Application No. 61/569,616 filed Dec. 12, 2011, both of which are incorporated herein in their entireties by reference.

FIELD OF THE INVENTION

The invention relates to systems, methods and devices for measuring blood-alcohol content. More specifically the invention relates to interactive, networked blood-alcohol content testing devices, systems and methods with self-clearing air chambers for high-volume usage.

BACKGROUND OF THE INVENTION

Alcohol consumption has been ever-present in the history of mankind. Humans began drinking alcohol in the early ages, in part, to combat the increasing pollution of the available drinking water. The distillation process involved in making alcohol cleansed many pollutants and provided a safe liquid for consumption. However, over time, the role of alcohol in society has changed and today, the consumption of alcohol is more recreational in nature. In addition to becoming more recreational, the consumption of alcohol has, at various stages, come under scrutiny and is subject to various forms of regulation. For example, from 1919 to 1933 the United States banned the sale, manufacture and transportation of alcohol for consumption. During these years this prohibition became very unpopular as the United States went through the Great Depression and the regulation was later repealed.

While the year 1933 marked the end of the outright ban on alcohol, regulations still exist today which affect how alcohol is consumed and distributed. For instance, there are limitations on the hours of the day that alcohol can be sold and on the acceptable blood-alcohol content (BAC) for performing various tasks such as flying an airplane, or operating a motor vehicle. Various reasons exist for the creation and maintenance of the regulations, including the adherence to precedent, and supportive research in the realms of economics and behavioral science. For example, studies have shown that alcohol may alter human behavior and impair judgment, reasoning, coordination and other basic human functions. In addition, some suggest that the consumption of alcohol contributes to significant losses in the economic, physical and emotional realms as addiction and overuse of alcohol may result in injuries to the workforce and society as a whole, either directly or indirectly.

The various regulations on alcohol consumption have created additional laws and regulations relating to liabilities of parties involved in accidents where a person was under the influence of alcohol. For example, certain states have enacted dramshop laws which establish that a bar or other alcohol-serving establishment may be liable for accidents arising out of the sale of alcohol to intoxicated persons who subsequently cause death or injury to others. In addition, there may be steep penalties for persons who are found to be exceeding the legal limits of BAC, such as fines, suspension of licenses and incarceration. Thus, irrespective of the basis for the various laws and regulations, their presence has created a need for devices that can measure BAC levels and provide consumers with information as to where they fall in relation to the regulations.

In response to the needs created by the laws and regulations, several companies have developed devices capable of detecting alcohol content in the blood. These BAC testing devices operate by analyzing the content of a breath sample to determine blood-alcohol content, and are often referred to as "breathalyzers". These breath-sampling BAC testing devices are commonly carried by law enforcement personnel and medical personnel in order to determine whether persons are in violation of the various laws and regulations, or to adjust medical service. In addition, such devices are available to consumers who may be interested in determining their BAC and ensuring they are within the legal limits.

In addition to usage by law enforcement and medical personnel, owners of various establishments that sell or serve alcoholic beverages have begun installing BAC testing devices as a benefit to their customers. However, such "commercial-class" BAC testing devices typically require regular monitoring and maintenance, presenting additional burdens to the owners of such devices.

Further, BAC testing devices located in bars and restaurants often administer multiple BAC tests in a relatively short period of time. As alcohol residue and moisture build up in such units, the accuracy of the BAC test results tend to diminish, such that only by waiting extended periods of time between uses can the user be assured that alcohol residue and moisture from previous users has dissipated, allowing for a more pure sample.

SUMMARY OF THE INVENTION

Embodiments of the present invention solve these deficiencies of known BAC test devices by providing BAC testers that not only rapidly and efficiently clear themselves, but also communicate over a network such that their operation can be monitored by remote personnel.

In an embodiment, the present invention comprises a blood-alcohol content (BAC) tester for use at a facility serving alcohol. The BAC tester comprises: a breath-sampling unit, the breath-sampling unit including: an air-chamber unit defining a closed position and an open position, the air-chamber unit having a first air-chamber block and a second air-chamber block, the first air-chamber block and the second air-chamber block defining an air chamber for receiving air exhaled from a user; a drive unit operably coupled to the second air-chamber block; an alcohol sensor for sensing the presence of alcohol in the air exhaled from the user; a sensor circuit communicatively coupled to the drive unit and the alcohol sensor; and an enclosure substantially enclosing the breath-sampling unit and the sensor circuit. Further, the sensor circuit is configured to cause the drive unit to move the second-air chamber block relative to the first air-chamber block so as to cause the air-chamber unit to be in the closed or the open position.

In another embodiment, the present invention comprises a method of measuring BAC using a BAC tester having an alcohol sensor, an air-chamber, and a display. The method includes: receiving from the user the user's estimate of the user's blood alcohol content; receiving in an air chamber exhaled air from a user of the BAC tester; measuring with the alcohol sensor an alcohol content of the air exhaled from the user of the BAC tester; determining an actual blood-alcohol content of the user of the BAC tester based on measurements of the alcohol sensor; and comparing the user's estimate of the user's blood alcohol content with the actual blood-alcohol content of the user.

In yet another embodiment, the present invention comprises an interactive BAC tester for connection to a remote-management system that includes a communications network and a remotely-connected server. The BAC tester comprises: an air-chamber configured to receive air exhaled from a user of the interactive BAC tester; an alcohol sensor coupled to the air chamber and configured to sample a portion of the air exhaled from the user of the interactive BAC tester; a sensor circuit communicatively coupled to the alcohol sensor and to receive a signal from the alcohol sensor, the signal indicative of an alcohol content of the air exhaled from the user and sampled by the alcohol sensor; a display configured to display selected information to the user of the interactive BAC tester; and a computer communicatively coupled to the sensor circuit and the display, the computer configured to communicate with a remotely-located computing device over a communication network. The computer is configured to transmit usage data indicating the number of times that the BAC tester was used over a predetermined time period, and configured to receive instructional data from the remotely-located computing device, the instructional data determining the selected information that is displayed by the computer on the display to the user of the interactive BAC tester.

BRIEF DESCRIPTION OF THE DRAWINGS

The invention can be understood in consideration of the following detailed description of various embodiments of the invention in connection with the accompanying drawings, in which:

FIG. 1b is a rear perspective view of the BAC testing device of FIG. 1a;

FIG. 3b is a front, right perspective view of the breath-sample capture portion of the BAC testing device of FIG. 3a;

FIG. 3c is a top view of the breath-sample capture portion of the BAC testing device of FIG. 3a;

FIG. 3d is a bottom, rear perspective view of the breath-sample capture portion of the BAC testing device of FIG. 3a;

FIG. 7a is a first portion of a flowchart depicting and describing an embodiment of the operation of the BAC testing device of FIGS. 1-6;

FIG. 8 is a depiction of a graphical user interface, according to an embodiment of the present invention;

FIG. 9 is a flowchart depicting and describing the blood-alcohol testing step of the flowchart of FIGS. 7a and 7b;

FIG. 15 is a flowchart depicting and describing the step of providing a reward of the flowchart of FIGS. 7a and 7b.

Figure 1A:
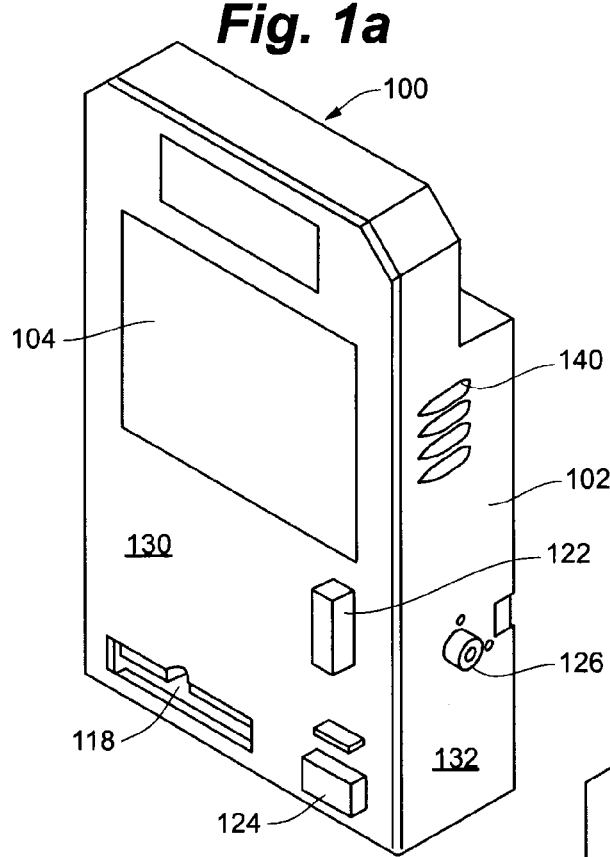
FIG. 1a is a front perspective view of a breath-sampling, blood-alcohol content (BAC) testing device, according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Figure 1B:
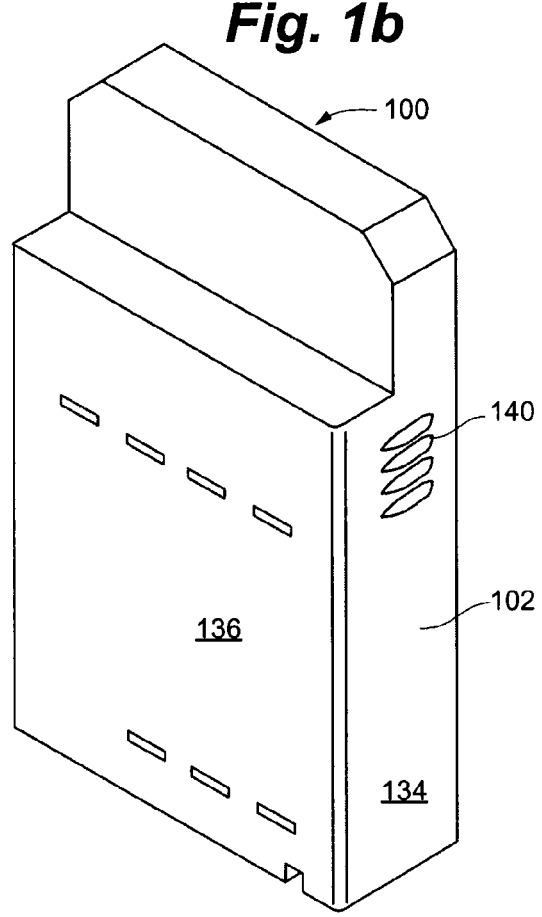
Figure 2:
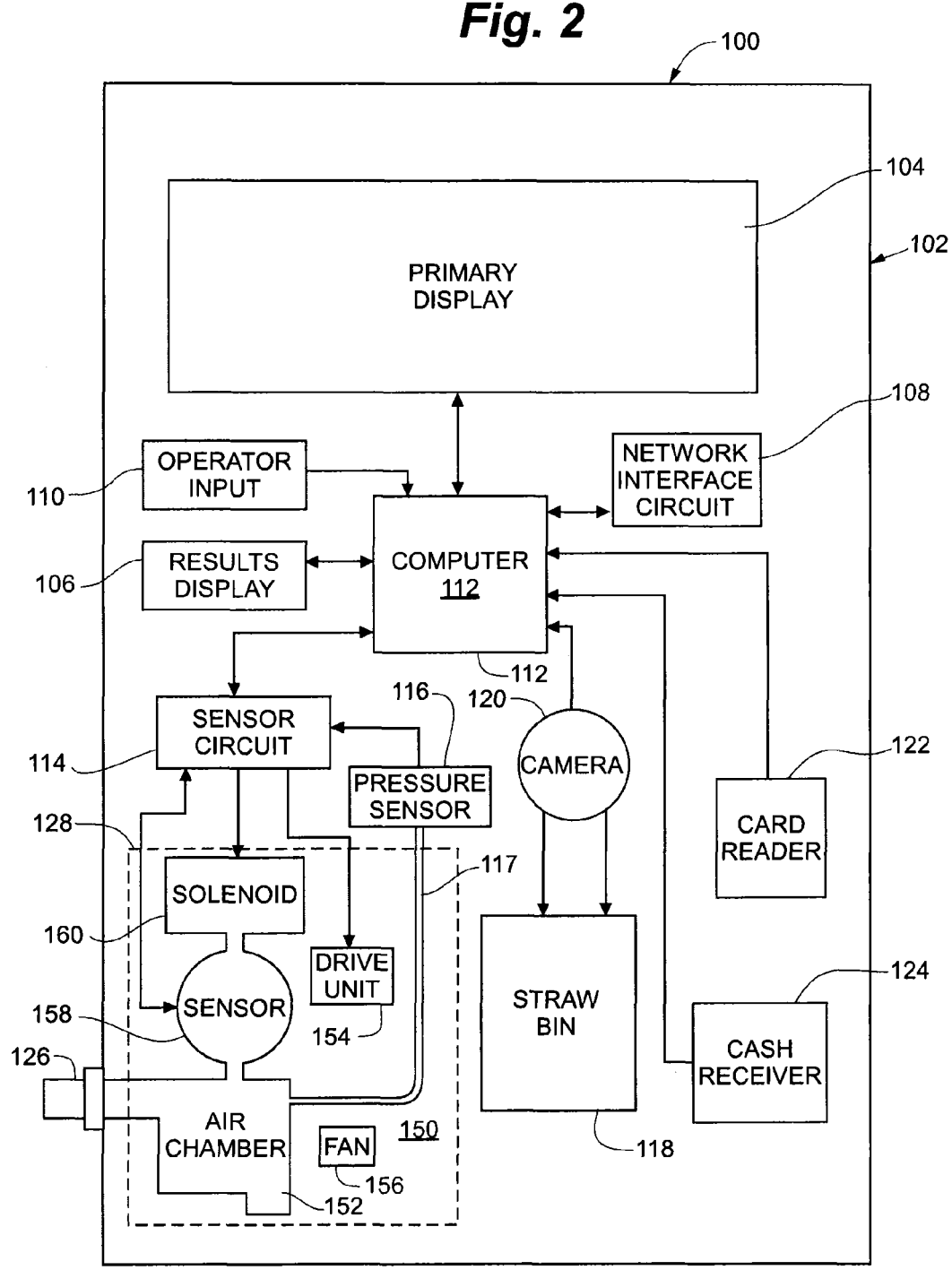
FIG. 2 is a block diagram of the BAC testing device of FIGS. 1a and 1b, according to an embodiment of the present invention.

Referring to FIGS. 1a, 1b, and 2, interactive blood-alcohol content (IBAC) tester 100 is depicted. In an embodiment, IBAC tester 100 includes enclosure 102, primary display 104, results display 106, network interface circuit 108, operator input 110, computer 112, sensor circuit 114, pressure sensor 116, straw bin 118, camera 120, credit card reader 122, cash receiver 124, straw receiver 126 and breath-sampling unit 128.

Referring specifically to FIGS. 1a and 1b, enclosure 102 includes front panel 130, right panel 132, left panel 134, and rear panel 136. Front panel 130 engages primary display 104, straw bin 118, credit card reader 122, and cash receiver 124, such that these items are accessible from a front side of IBAC tester 100. Right panel 132 and left panel 134 include vents 140. Right panel 132 also includes an opening to receive at least a portion of straw receiver 126. Straw receiver 126 projects out of panel 132. Enclosure 102 may also include an access door, which may be a locking door, for accessing components housed within. Enclosure 102 may also include a light enclosed within housing 102.

In an embodiment, enclosure 102 includes graphic designs on front panel 130, which may include instructional information, advertising, and so on.

Referring also to FIG. 2, a block diagram of IBAC tester 100 is depicted. Primary display 104 in an embodiment comprises an interactive touch-screen display. Primary display 104 displays a graphical user interface (GUI) to a user of interactive BAC tester 100. As will be described further below, the GUI may display various icons, widgets, and other information to the user. When embodied as a touch-screen display, primary display 104 not only displays the GUI to a user, but also receives input from a user touching the touch-screen display, as will be understood by those skilled in the art. Primary display 104 is communicatively coupled to computer 112.

In an embodiment, IBAC tester 100 also includes results display 106. Results display 106 may be any of known displays, such as an LCD or LED display, a touch-screen display, and so on. In an embodiment, results display 106 is dedicated primarily to displaying a blood-alcohol content (BAC) test result to a user. In other embodiments, a BAC test result may be displayed on primary display 104, or on both displays. Results display 106 may also be in communication with computer 112 and/or sensor circuit 114.

Network interface circuit 108 is communicatively coupled to computer 112. Network interface circuit 108 includes hardware and/or software to provide an interface to an external network, such as the network depicted in FIG. 6. Network interface circuit may be integral to computer 112.

Operator input 110 includes devices or structures for receiving input from a user of IBAC tester 100. In one embodiment, operator input comprises a series of buttons or keys. Such buttons or keys may be hardware, or may be virtual buttons or keys as provided on a display. In another embodiment, user input 110 may comprise a voice-exchange system. Operator input 110, or portions thereof, may be accessible from the outside of IBAC tester 100, for example, protruding through front panel 130. In other embodiments, all of, or portions of operator input 110 may be located inside enclosure 102, such that only authorized users, such as an operator, owner, or maintainer of IBAC tester 100, may be allowed to access all or portions of operator input 110.

Computer 112, as understood by those skilled-in-the-art, may include a processor, microcomputer, microcontroller, or other such computing or processing device. Computer 112 may also include volatile and/or non-volatile memory devices for storing data and/or software relating to the operation of IBAC tester 100. Computer 112 is communicatively coupled to various components of IBAC tester 100, which may include, but not be limited to, primary display 104, results display 106, network interface circuit 108, operator input 110, sensor circuit 114, camera 120, credit card reader 122, and cash receiver 124. In an embodiment, computer 112 is also communicatively coupled to various components of breath-sampling unit 128.

Sensor circuit 114 is communicatively coupled to breath-sampling unit 128 and pressure sensor 116, and includes hardware and/or software for operating breath-sampling unit 128, including capturing user-generated breath-air samples, determining user BAC, clearing breath-sampling unit 116, and other such functions as described further below. In an embodiment, the hardware of sensor circuit 114 may include a power-conditioning circuit, a processor and memory for storing data and software related to the above-described functions.

Pressure sensor 116 is communicatively coupled to sensor circuit 114 and senses pressure in an air chamber of breath-sampling unit 128. Pressure sensor 116 may be a sensor that measures, detects, or senses absolute pressure, or changes in relative pressure.

Straw bin 118 retains straws, or other similar such items used to couple a user's mouth to IBAC tester 100, such that IBAC tester 100 may receive exhaled air from a user. Straw bin 118 may be primarily located within enclosure 102, with an external, or exposed, portion accessible to a user for retrieving a straw. Straw bin 118 may dispense straws automatically on a per test basis, or may rely on gravity to allow straws to be accessible to a user. In an embodiment, straw bin 118 is partially visible through a frame opening in enclosure 102.

In an embodiment, IBAC tester 100 includes camera 120. Camera 120 views straw bin 118 and its straws, and is communicatively coupled to computer 112.

Credit card reader 122 is accessible through front panel 130 so that a user may swipe a credit card to make payment for using IBAC 100. Card reader 122 is in communication with computer 112, which in turn is in communication with a credit card processing or verification service or company, via an external network (see also FIG. 6).

Cash receiver 124 also is accessible through front panel 130, and as will be understood by those skilled-in-the-art, is configured to receive a cash payment from a user. In an embodiment, cash receiver 124 is a bill acceptor that receives and reads paper money. In another embodiment, cash receiver 124 may accept coins in addition to, or instead of, bills. Cash receiver 124 is in electrical communication with computer 112 and/or sensor circuit 114.

Straw receiver 126 as depicted is located at a side of IBAC tester 100, at right panel 132, and is adapted to receive a straw inserted by a user. Alternatively, straw receiver 126 may be located elsewhere on IBAC tester 100, such as at left panel 134, or front panel 130. Straw receiver 126 defines an opening sized to receive an end of a straw, such as a straw from straw bin 118.

Referring also to FIGS. 3a to 3d, an embodiment of breath-sampling unit 128 is depicted. Breath-sampling unit 128 includes air-chamber unit 150 defining air chamber 152, drive unit 154, fan 156, fuel-cell sensor 158, solenoid unit 160, first guide post 161 and second guide post 163. Breath-sampling unit 128 is generally located within enclosure 102, is coupled to straw receiver 126 at air chamber 152. Fuel cell sensor 150 is coupled to air chamber 152, while solenoid unit 160 is coupled to fuel cell sensor 158.

In the embodiment depicted, air-chamber unit 150 includes first air-chamber block 170 and second air-chamber block 172. Together, first air-chamber block 170 and second air-chamber block 172 define air chamber 152. When air-chamber unit 150 is in a closed position, second air-chamber block 172 is adjacent first air-chamber block 170, as depicted. First air-chamber block 170 and second air-chamber block 172 are described further below with respect to FIGS. 4 and 5.

Drive unit 154 includes motor 180, drive shaft 182, and block coupler 184. Motor 180 comprises an electric motor in electrical communication with sensor circuit 114. Drive shaft 182 is coupled to motor 180 and block coupler 184. Drive shaft 182 extends generally perpendicularly from motor 180 and through block coupler 184. In an embodiment, drive shaft 182 comprises a threaded rod or screw. The threads may extend the entire length of drive shaft 182, or only part of the length. In other embodiments, drive shaft 182 may comprise other types of shafts or gears for engaging block coupler 184.

In an embodiment, block coupler 184 includes disc 186, shaft engaging portion 188, fasteners 190, and springs 192.

Disc 186 is located adjacent an end of shaft-engaging portion 188, and forms a generally plate-like, or disc-shaped structure having an opening in the center through which drive shaft 182 may extend. In an embodiment, the center opening of disc 186 is threaded so as to engage drive shaft 182. In another embodiment, the center opening of disc 186 is not threaded and does not substantially engage drive shaft 182.

Disc 186 supports fasteners 190 which generally extend perpendicularly away from disc 186 toward second air-chamber block 172. Fasteners 190 are spaced equidistant from the center of disc 186 and from each other. Fasteners 190 engage second air-chamber block 172. In an embodiment, fasteners 190 comprise threaded bolts or screws that penetrate a portion of second air-chamber block 172. Springs 192, when included, fit over fasteners 190 and are compressed or decompressed as fasteners 190 are adjusted into and out of second air-chamber block 172, thusly providing a biasing force on disc 186 in a direction away from surface 194 of second air-chamber block 172.

The combination of disc 186, fasteners 190 and springs 192 engaging second air-chamber block 172 distributes forces imparted to second air-chamber block 172 from drive shaft 182 while drive unit 154 causes second air-chamber block 172 to move toward and away from first air-chamber block 170 along guide posts 161 and 163, as will be described further below. This structure allows second air-chamber 172 to travel consistently in a direction along an axis defined by drive shaft 182 such that surface 240 of second air-chamber block 172 is generally maintained parallel to surface 216 of first air-chamber block 170, and second air-chamber block 172 does not bind against guide posts 161 and 163 (also see FIGS. 4 and 5).

Shaft-engaging portion 188, in an embodiment, comprises a generally cylindrical structure defining a central threaded passage for receiving and engaging drive shaft 182. Shaft-engaging portion 188 engages disc 186 at a top surface of shaft-engaging portion 188 and a bottom surface of disc 186. Shaft-engaging portion 188 engages second air-chamber block 172 and an outer surface 194. As such, shaft-engaging portion 188 is adjacent, and between, disc 186 and second air-chamber block 172.

Fan 156, as described further below, is an electrically-power fan controlled by sensor circuit 114 for blowing air to clear air chamber 152 when air-chamber blocks 170 and 172 are separated. In an embodiment, fan 156 comprises an axial-flow fan that includes a fan motor turning a plurality of blades to create an air flow.

Fan 156, as depicted, is mounted adjacent and transverse to first air-chamber block 170 via pillars 196 such that airflow is directed generally parallel to inside and outside surfaces of blocks 170 and 172, including surface 194. Fan 156 may be located elsewhere in other embodiments, while still causing air to be directed towards air chamber 152.

Fuel-cell sensor 158, as will be understood by those skilled-in-the-art, comprises a sensor for detecting and measuring alcohol content in an air sample, such as breath or air exhaled by a user of IBAC tester 100. As will also be understood by those skilled in the art, fuel-cell sensor 158 includes an electrode that receives breath air from a user and outputs an electrical current and/or corresponding voltage commensurate with the level of alcohol in the sampled air. Fuel-cell sensor 158 may comprise any of well-known commercially-available fuel-cell sensors, including fuel-cell sensors as manufactured by PAS Systems International, Inc. of Fredericksburg, Va.

Solenoid unit 160 includes solenoid actuator 200, plenum 202, and support plate 204. Solenoid actuator 200 is mounted to support plate 204 and is operatively connected to plenum 202. Support plate 204 is coupled to first air-chamber block 170. Plenum 202 is coupled to fuel-cell sensor 158.

Solenoid actuator 200, in an embodiment, comprises an electrically-activated electromechanical device that moves an internal plunger, which as described further below, creates a vacuum in plenum 202, drawing air through fuel-cell sensor 158. Solenoid actuator 200 receives a control signal from sensor circuit 114, which in some embodiments, will comprise a command from a processor of sensor circuit 114.

Figure 4:
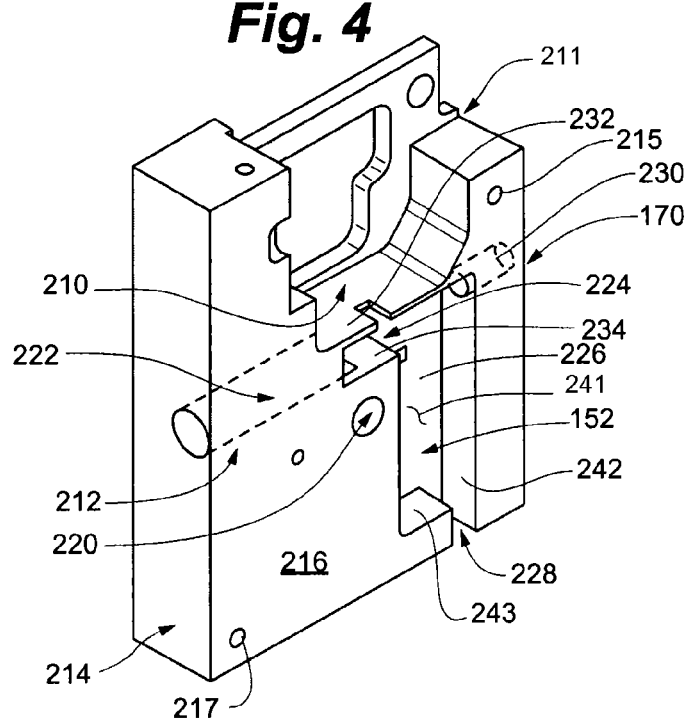
FIG. 4 is a front perspective view of a first air-chamber block, according to an embodiment of the present invention.
Figure 5:
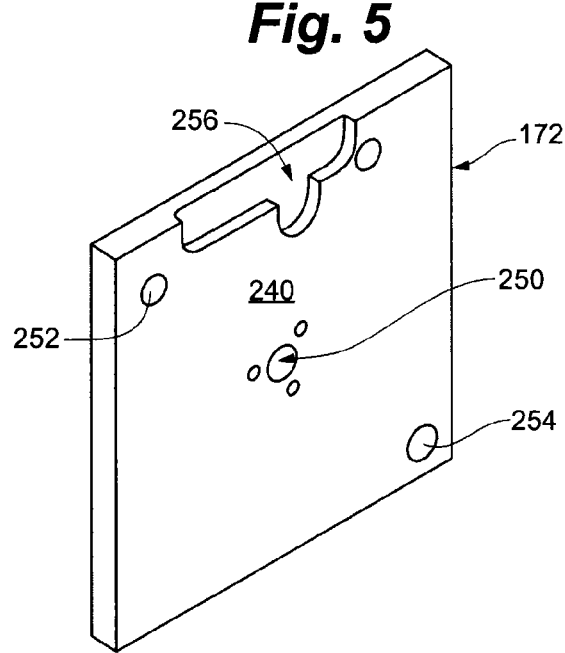
FIG. 5 is a front perspective view of a second air-chamber block, according to an embodiment of the present invention.

Referring specifically to FIG. 4, in the embodiment depicted, first air-chamber block 170 may form a generally square shape defining one or more cavities, including a cavity forming a portion of air chamber 152. First air-chamber block 170 may be formed of a single piece of material, with portions of the material removed to form the particular shape of first air-chamber block 170. In other embodiments, first air-chamber block 170 is an assembly formed of multiple portions assembled together.

Figure 3A:
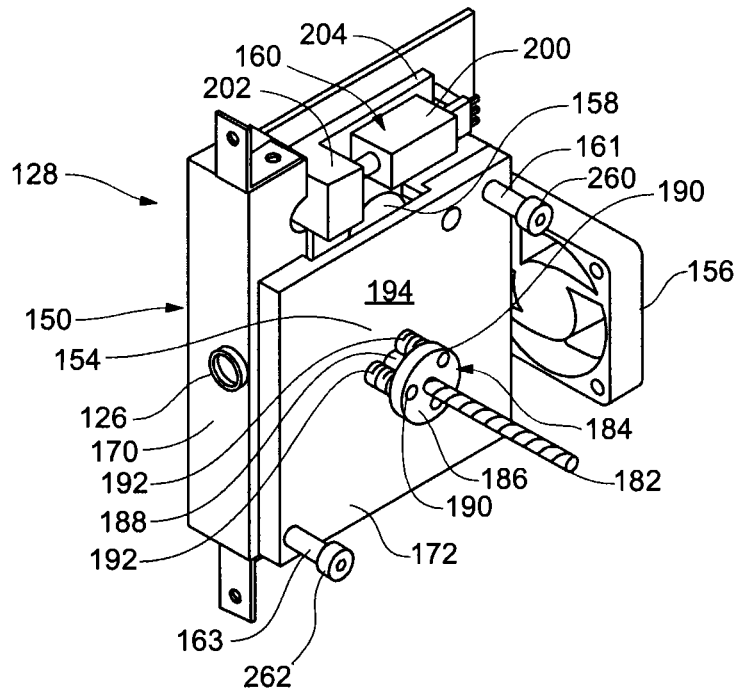
FIG. 3a is a front, left perspective view of a breath-sample capture portion, in a closed position, of the BAC testing device of FIGS. 1a and 1b, according to an embodiment of the present invention.
Figure 3B:
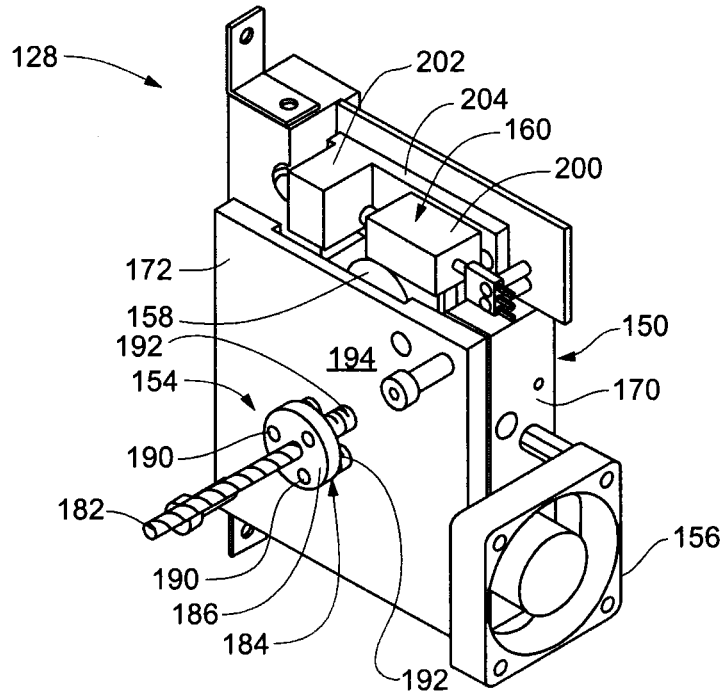
Figure 3C:
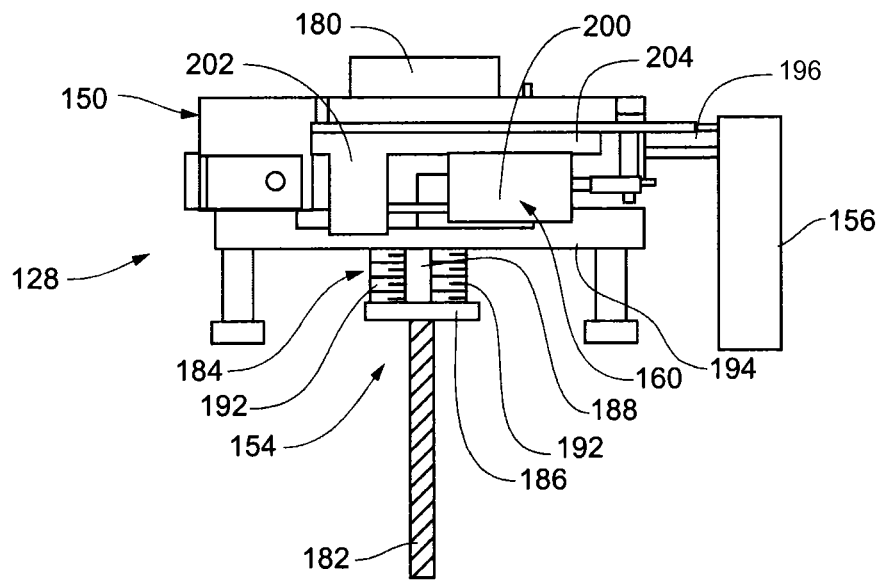
Figure 3D:
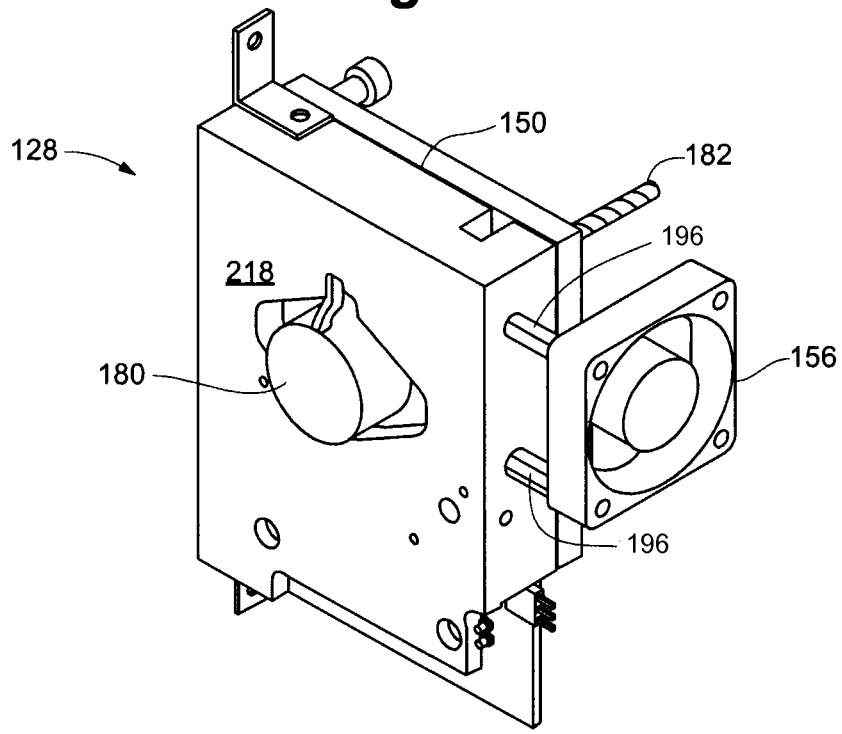

First air-chamber block 170 includes an upper portion 210, central portion 212, lower portion 214, inner surface 216 and outer surface 218 (see also FIG. 3*d*). An upper portion 210 of first air-chamber block 170 defines upper recess 211 for receiving solenoid unit 160. Central portion 212 defines a drive-shaft aperture for receiving drive shaft 182. Central portion 212 and lower portion 214 together define air chamber 152. First air-chamber block 170 also includes first guide-post receiving aperture 215 and second guide-post aperture 217 for receiving first and second guide posts 161 and 163, respectively.

Air chamber 152 in an embodiment defines a generally L-shape, though it will be understood that in other embodiments, air chamber 152 may define other shapes dependent in part upon a desired inlet and outlet of the air-chamber 152 is defined by inlet portion 222, horizontal portion 224, vertical portion 226, outlet portion 228, and pressure-test channel 230.

Inlet portion 222 defines a channel extending from an outside, left side of first air-chamber block 170, through a portion of first aid-chamber block 170 and into horizontal portion 224. Horizontal portion 224 is defined by dividing wall 232, step 234, central back wall 241 of first air-chamber block 170 and inside surface 240 of second air-chamber block 172 (see also FIG. 5). Vertical portion 226 is defined by central portion 212, surface 242 of a right-side of first air-chamber block 170, step 243, and central back wall 240 of second air-chamber block 172.

Second air-chamber block 172 in the embodiment depicted comprises a generally square, flat plate-like structure. Second air-chamber block 172 includes generally planar inner surface 240 and outer surface 194 (see also FIGS. 3*a* and 3*b*). In alternate embodiments, second air-chamber block 172 may define cavities or recesses that form a portion of air-chamber 152.

Second air-chamber block 172 defines drive-shaft aperture 250 for receiving drive shaft 182. Second air-chamber block 172 also defines a first guide-post aperture 252 and a second guide-post aperture 254. As depicted, second air-chamber block 172 may also define recess 256 for receiving a portion of fuel-cell sensor 158 or a portion of solenoid unit 160, when in the closed position adjacent first air-chamber block 170.

When assembled into air-sampling unit 128, and in the closed position, surface 240 of second air-chamber block 172 contacts surface 216 of first air-chamber block 170, thusly closing air-chamber 152. In some embodiments, a gasket may be used between surfaces 216 and 240, though generally a gasket is not required.

Referring also to FIGS. 3*a* to 3*d*, first guide post 161 is affixed to first air-chamber block 170 at first guide-post receiving aperture 215, while second guide post 163 is affixed to first air-chamber block 170 at second guide-post receiving aperture 217. In an embodiment, first guide post 161 includes a first end that is threaded so as to turn or screw into first guide-post receiving aperture 215; second guide post 161 includes a first end that is also threaded so as to turn into second guide-post receiving aperture 217. In an embodiment, first guide post 161 includes a second end having a flange 260; second guide post 163 includes a second end having a flange 262.

First guide post 161 is received by first guide post aperture 252 and passes through second air-chamber block 172; second guide post 163 is received by second guide post aperture 254 and also passes through air-chamber block 172. As such, second air-chamber block 172 is slidably coupled to first air-chamber block 170 via guide posts 161 and 163. In other embodiments, IBAC tester 100 may include more than two guide posts, and guide posts may be located in other positions about first and second air-chamber blocks 170 and 172.

Figure 6:
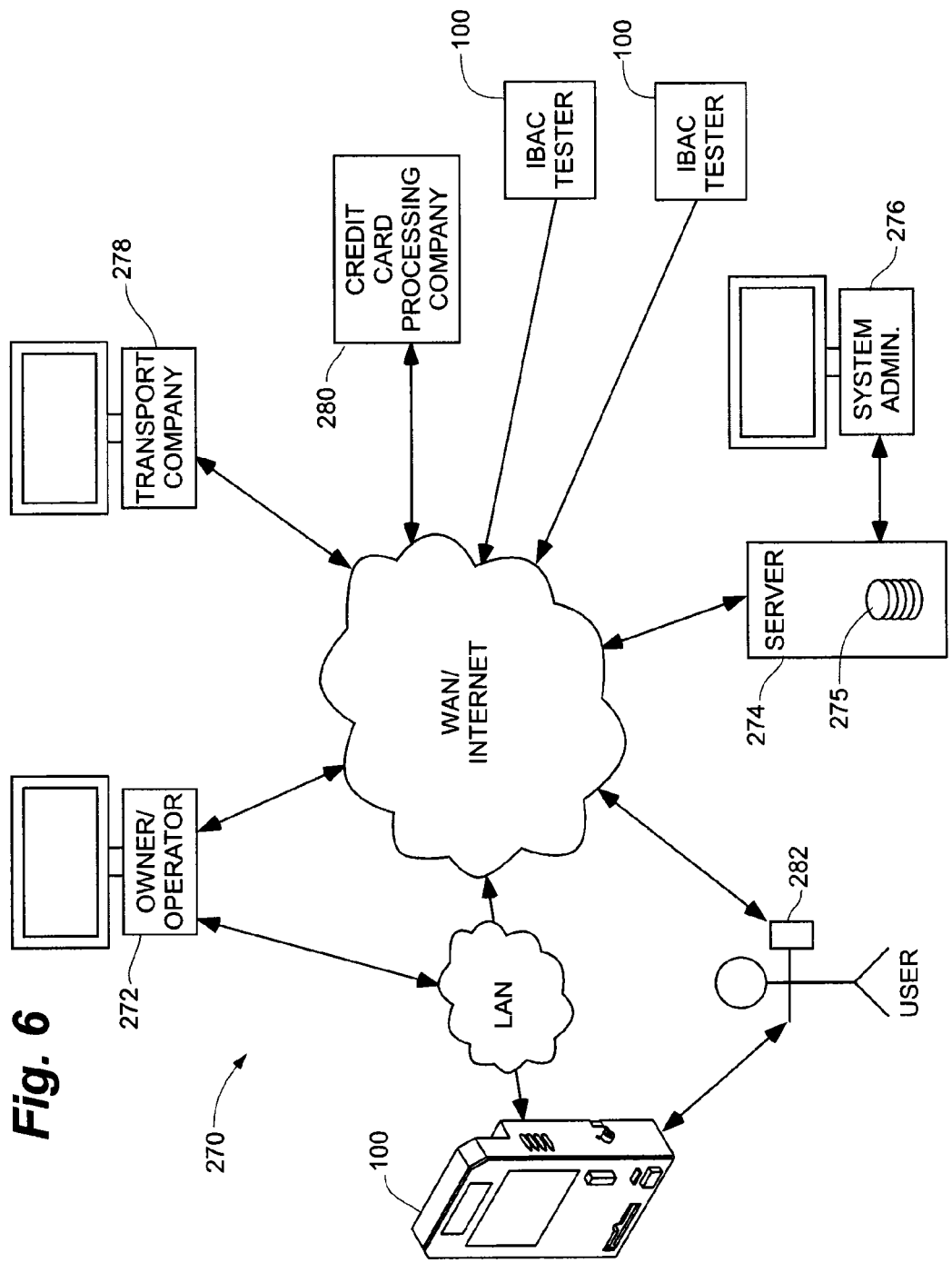
FIG. 6 is a network diagram of BAC testing device and system, according to an embodiment of the present invention.

Referring to FIG. 6, in an embodiment, IBAC tester 100 may be connected to a local-area network (LAN) and/or a wide-area network (WAN) to comprise remote-management system 270. The WAN may include the Internet.

System 270 may include one or more IBAC testers 100, an optional LAN, owner/operator 272, server 274 in communication with system administrator 276, transportation company 278, credit card processing company 280, and to a certain extent, a user operating mobile device 282. Other authorized entities may also connect to system 270 via the WAN. In an embodiment, each IBAC tester 100 connected to the Internet is assigned its own Internet protocol (IP) address.

An owner/operator 272 may be the owner or proprietor of the facility where IBAC tester 100 is located, but more typically, an owner/operator may not own the facility, but rather provides, services, and maintains the equipment. In such an instance, the owner/operator would not typically be at the facility on a regular basis.

A LAN may exist at the facility where IBAC tester 100 is located, such that IBAC tester 100 connects to the WAN or Internet through network interface equipment of the LAN located at the facility. However, it will be understood that although in some embodiments a LAN may be present, in other embodiments it is not. Further, it will also be understood that while embodiments of IBAC tester 100 may be connected to a LAN or WAN, the tester could conceivably be operated independently of any network connections.

System administrator 276 administers server 274 and system 270. Server 274 stores software and data relevant to the operation of the network and any IBAC testers 100 connected to the network. Data from IBAC testers 100 may be collected and stored in a database 275 on one or more servers 274. As will be understood by those-skilled-in-the-art, server 274 comprises memory devices for storing such data and software, as well as one or more processors. In an embodiment, server 274 operates as a MySQL® server and database.

System administrator 276 may have the capability to remotely control various functions of each IBAC tester 100 in the network. Such functions may include control of ad content, ad timing and sequencing, GUI changes, general operability, data collection, report generation, and so on. Generally speaking, all relevant content may be stored, accessed, and manipulated through server 274 by system administrator 276.

In an embodiment, remote access to each IBAC tester 100, by system administrator 276 or owner/operator 272, may be facilitated by software and hardware, including Windows®7 remote-access gateway. In such a configuration, system administrator 276, owner/operator 272, or other authorized person having access, may "enter" any IBAC tester 100 in the network to create a virtual presence at IBAC tester 100. This ability allows access to additional information and to perform a number of additional functions, such as viewing straw bin 118 through camera 120, monitor programming and/or operation of IBAC tester 100, and trouble shooting software issues that may arise.

Consequently, the system administrator can log into the system and perform a number of functions such as:

Adding new IBAC testers 100 to the network. In an embodiment, each IBAC tester 100 is assigned an IBAC tester number, which allows remote management system 270 to differentiate one tester from another. By using the tester number, each tester is tied to its respective geographic territory and facility address. Once an IBAC tester 100 is added to the network/system, it can be monitored from any computer with an internet connection and proper authorization.

Creating a new operator. The administrator creates a username and password for each new IBAC tester 100 owner/operator 272.

Creating, editing, or deleting new advertisements. Ads that cycle through on the touch screen monitor when the IBAC tester 100 is not being used can be added or removed from any IBAC tester 100 throughout remote management system 270. This is done by first creating a new advertisement group in the advertising control screen. An advertisement group is created with a preset loop of ads that are intended to be displayed on IBAC testers 100 in one or more locations. In an embodiment, system administrator 276 can manipulate this content at any time. Any number of IBAC testers 100 can be part of an ad group.

Matching each IBAC tester 100 to a user and ad group. System administrator 276 can set up remote management system 270 so that an operator 272 of each IBAC tester 100 can view and manage their own IBAC testers 100 but cannot gain access to any other IBAC testers 100 in the network or system. The control is set up so that operators 272 can be tracked in a central-control program, and owner/operator 272 can view only those IBAC testers 100 associated with that particular owner/operator 272. Similarly, in an embodiment, an operator can only view the advertisements applied to their testers, but cannot edit them. System administrator 276 can change the operator or ad group matched to an IBAC tester 100 at any time.

Monitoring straw levels. As described above, camera 120 may be positioned above straw bin 118 allowing owner/operator 272 to monitor straw levels and to anticipate when a refill may be needed. Owner/operator 272 can access camera 120 and view the straw level through remote management system 270 to determine if a new supply of straws needs to be added to straw bin 118.

Monitoring fuel-cell sensor 158 life. When fuel-cell sensor 158 is starting to wear out, a signal is sent from sensor circuit 114 or computer 112 to operator 272 or system administrator 276, indicating that it is time for an existing fuel-cell sensor 158 to be replaced by a new sensor.

In an embodiment, every day, an automated, scheduled task synchronizes each IBAC tester 100 software application via remote management system 270. All IBAC tester 100 data is updated on a website administered through remote management system 270. All changes to ad content on the website are updated on each designated IBAC tester 100.

An owner/operator 272 can log onto the remote monitoring website with the username and password assigned to them. The logged-in operator can then view the list of IBAC testers 100 associated with, or assigned to, that particular operator. Each IBAC tester 100 will display how many times it has been used. The number of credit card readings, bill acceptor uses, or activation code uses may also be tracked and reported. With these statistics, the operator can monitor cash box levels and anticipate when each cash box should be emptied. The operator can also see what ads are playing on what tester, and how many times each ad has played.

As will be described further below, remotely-located credit card processing company 280, may also be in communication with IBAC testers 100 to facilitate processing of credit cards used to purchase BAC tests administered by connected IBAC testers 100.

As will also be described further below, remotely-located transportation companies 278 may also connect to the network to communicate with IBAC testers 100 and in some embodiments, with users' mobile devices 282, so as to arrange transportation for a user.

Owner/operators can also remotely monitor operation, being alerted to errors or problems related to operation of IBAC tester 100. Further, the need for servicing, or even routine maintenance can be communicated via the WAN to owner operator 272 by IBAC tester 100, or in some embodiments, by system administrator 276.

In some embodiments, owner/operator 272 may also update or modify the interface, or graphics, displayed on primary display 104, though in other embodiments these operations may be handled exclusively by system administrator 276.

Generally speaking, remote management system 270 provides the ability to remotely manage and maintain multiple IBAC testers 100 connected to the network, thereby minimizing the required number of physical visits to IBAC testers 100. Further, remote management system 270 enables an owner/operator 272 to file and organize usage, advertisement, and component statistics.

As such, the remote management system 270 enables owner/operators 272 to monitor any and all IBAC testers 100 in their network from any PC or laptop computer. Remote management system 270 can track payments (both dollar bills and credit cards), monitor straw levels, view the monitor image in real time on any unit, check for operational problems and resolve most problems remotely, load advertising, load program updates, check the sensor, and perform other basic functions for all networked IBAC testers 100 across the country or around the world.

Figure 7B:
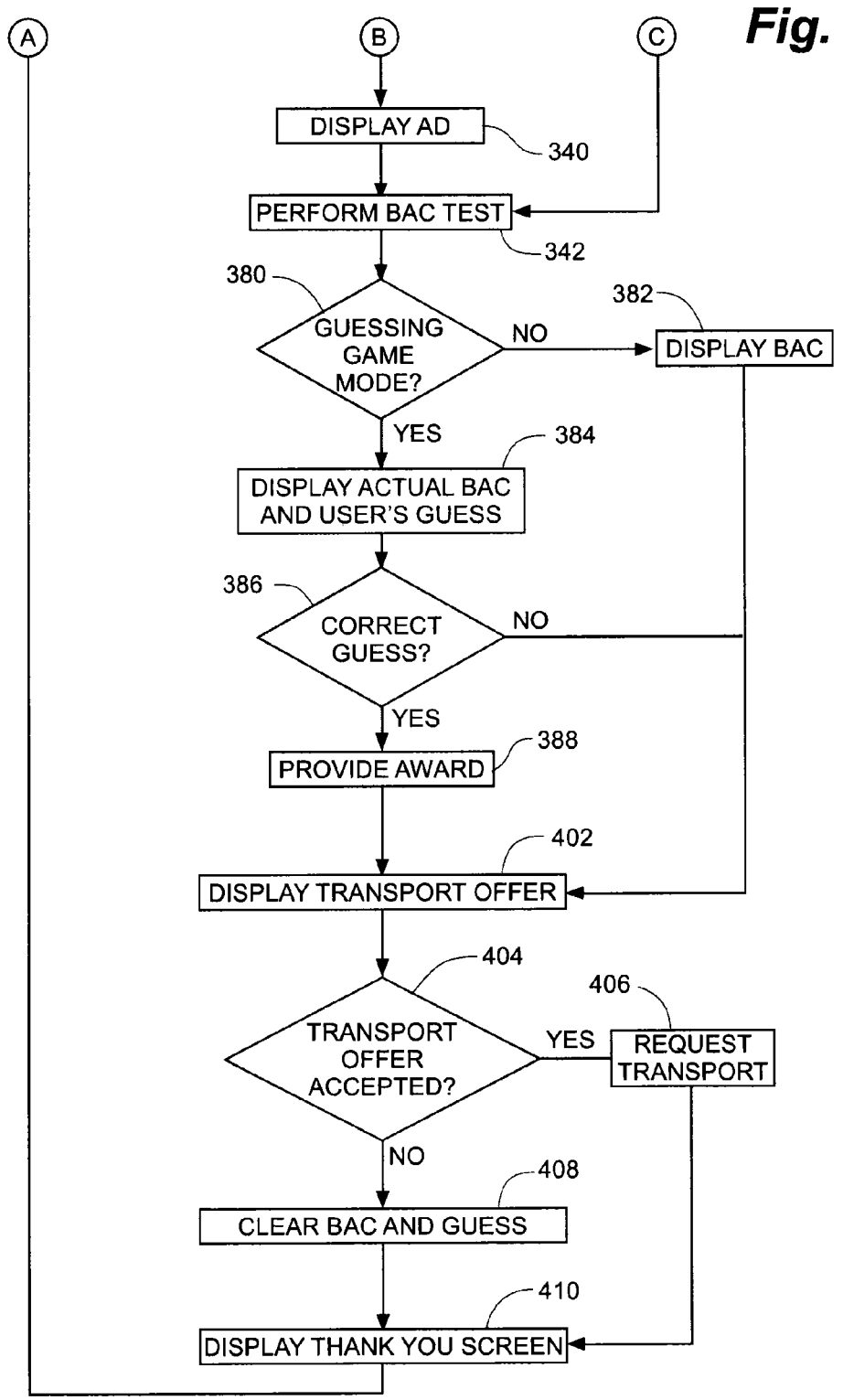
FIG. 7b is a second portion of a flowchart depicting and describing an embodiment of the operation of the BAC testing device of FIGS. 1-6.

Referring to FIGS. 7a and 7b, the general operation of IBAC tester 100 is depicted and described.

Referring to FIG. 7a and FIG. 2, prior to testing, at step 300, IBAC tester 100 displays advertisements on primary display 104. In an embodiment, multiple ads may be displayed in cyclical fashion. Ad content may be stored locally in computer 112, or may be transmitted in real-time via a local-area or wide-area network, such as the network depicted in FIG. 6.

An advantage of IBAC tester 100 being connected to a network, such as the network depicted in FIG. 6, is that ads can be managed remotely. Ads can be added or dropped on any ad loop or in-use ad in the network. A specific ad can be loaded onto every IBAC tester 100, just a few IBAC testers 100, or on a selected individual IBAC tester 100. In an embodiment, and for the benefit of advertisers, a proof of play section displays how many times each ad has been played on each IBAC tester 100.

At step 302, if a user is not requesting a test, ads continue to be displayed and cycled on primary display 104, as indicated at step 300. In an embodiment, a user requests a test by touching primary display 104, which may be a touch screen device. If a user is requesting a test, in an embodiment, primary display 104 ceases to display ads, and instead displays a welcome screen to the user, according to step 304.

An embodiment of welcome screen 306 is depicted in FIG. 8. As depicted, welcome screen 306 includes four virtual buttons, three corresponding to payment options, and one corresponding to a request for transportation. The three payment buttons include credit/debit card button 308, cash button 310 and activation code 312. As described below, in an embodiment, IBAC tester 100 may offer and accept activation codes that permit a user to receive a free or discounted BAC test.

In an embodiment, welcome screen 306 also includes cab call or transportation request button 314. As will be described further below, the transportation request button 314 allows a user to request a cab or other such transport by simply touching the transportation request button 314.

A user may select the type of payment by touching display 104 at one of buttons 308, 310 or 312. In other embodiments, particularly those in which display 104 does not comprise a touch-screen device, a user may select a payment type by depressing physical buttons of IBAC tester 100, by speaking a command, or by other such methods of selection.

After receiving the user-payment selection at step 318, in an embodiment, IBAC tester 100 may display one or more notice screens at step 320. One notice may advise that drinking within several minutes of testing will distort the accuracy of the test. Another notice screen may be a disclaimer or waiver that informs the user that IBAC tester 100 is for educational purposes only, and that test results cannot be used as evidence in a court of law. In an embodiment, for the test to continue, the user must agree to the terms and conditions displayed.

After receiving confirmation that the user agrees to the terms and conditions, the payment process continues at step 322.

At step 324, if the user selects the payment option of a credit or debit card, the credit card is processed at step 326. As part of this process, IBAC tester 100 may prompt the user to swipe a credit card through credit card reader 122. Referring also to the network diagram of FIG. 6, IBAC tester 100 transmits the received credit card information to credit card processing company 280 via remote management system 270 and the Internet. If credit card processing company 280 approves the transaction, the process continues to step 334.

At step 324, if the user selects the payment option of cash, the user inserts cash into cash receiver 124 and the process continues to step 334.

At step 332, if the user selects the activation code option, IBAC tester 100 via display 104 provides instructions for entering the activation code, a series of alphanumeric characters, such that the subsequent BAC test is administered for free.

At step 334, an option of a guessing game or a quick test is displayed. If the quick test is selected, rather than the guessing game, the process advances to step 342. If the guessing game is selected, a user guesses or predicts his/her blood-alcohol content for the opportunity to receive a reward, which in an embodiment is an activation code for a free BAC test.

If the user opts for the guessing game, IBAC tester 100 at step 338 receives the user's BAC guess. In an embodiment, IBAC tester 100 prompts the user to input his BAC prediction via a keypad displayed via primary display 104.

In an embodiment, the user is offered a BAC prediction or guess ranging from 0.00 to 0.30. After selecting or guessing a BAC level, the user's guess is stored in memory for future reference and display.

The "guessing game" or BAC prediction option serves multiple purposes. First it makes the process of testing BAC more enticing and interesting, thusly attracting more usage. Secondly, studies indicate that when a user reflects upon his/her own level of intoxication before being informed of the actual BAC test results, the user becomes better at predicting his/her BAC results, thereby increasing his awareness of his level of intoxication.

In an embodiment, ads are displayed periodically throughout the process, including at step 340.

At step 342 the BAC test is performed.

Referring now to FIG. 9, details of step 342, performing the BAC test, are depicted and described.

At step 344, the process of sampling air exhaled from the user and subsequent testing of the exhaled air is initiated. In an embodiment, the process is initiated by having the user depress a button of operator input 110 to initiate the BAC testing sequence.

At step 346, air chamber 152 of breath-sampling unit 128 is closed. Referring back to FIGS. 3a to 3d, breath-sampling unit 128 is depicted in the closed position. Air chamber 152 is "closed" when first air-chamber block 170 is adjacent second air-chamber block 172, as depicted.

Referring again to FIG. 9, at step 348, IBAC tester 100 displays instructions to the user regarding how to conduct the BAC test. Generally, the user is instructed to retrieve a straw from straw bin 118, insert the straw into straw receiver 126, take a deep breath, and exhale into the straw.

At step 350, IBAC tester 100 receives the user's exhaled air (breath).

Figure 10:
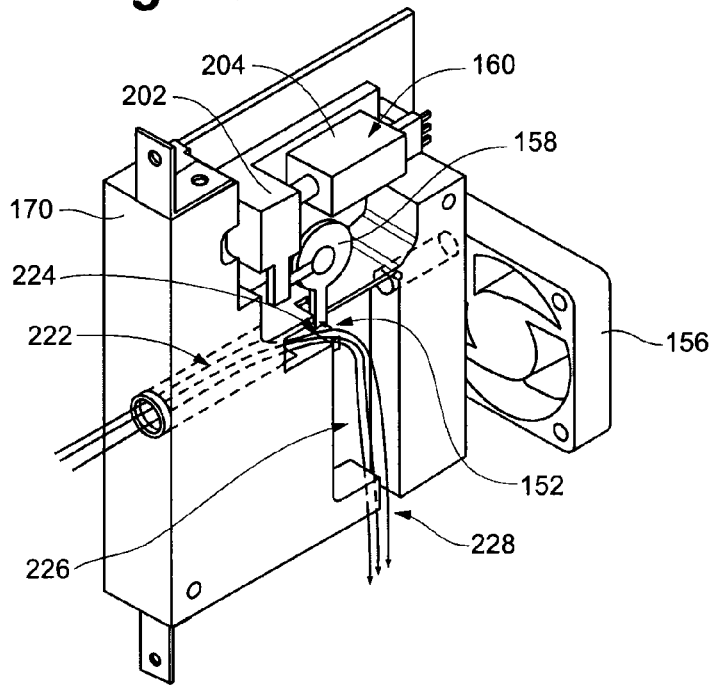
FIG. 10 is a partial view of the breath sample capture portion of FIGS. 3a-3d, depicting breath air flowing through the device.

Referring also to FIG. 10, upon exhaling through the straw, exhaled air, the user's breath, exits the straw and enters air chamber 152. FIG. 10 depicts breath-sampling unit 128 with second air-chamber block 172 and guide posts 161 and 163 removed. FIG. 10 also depicts the path of air exhaled from the user through air chamber 152, as indicated by the arrows.

Air exhaled from the user exits the straw and enters inlet portion 222. The air or breath travels along horizontal portion 224 of air chamber 152. The exhaled air then travels into horizontal portion 226 of air chamber 152, then exits air chamber 152 through outlet 228.

As the user exhales, and the exhaled air flows through air chamber 152, an air pressure inside air chamber 152 increases.

As described briefly above, pressure sensor 116 is connected to air chamber 152 via pressure-test channel 230, and in some embodiments by pressure-sense tube 117. Pressure sensor 116 senses the air pressure inside air chamber 152, and provides the data to sensor circuit 114. Sensor circuit 114 and/or its processor, monitors the sensed pressure in air chamber 152 while the user is exhaling, as indicated at steps 352 and 354 of FIG. 9.

When the air pressure within air chamber 152 begins to decrease as detected by pressure sensor 116, sensor circuit 114 sends a control signal to solenoid unit 160 causing an air sample from air-chamber 152 to be taken, as indicated at step 356, and as depicted in FIG. 10. By waiting until the pressure begins to decrease before taking a sample, IBAC tester 100 increases the probability that fuel-cell sensor 158 samples air taken at the end of the user's exhale cycle. This sampled air is often referred to as "deep-lung air", and provides a more accurate sample for determining the user's BAC step 358.

As will be understood by those skilled-in-the-art, solenoid unit 160 receives an electrical control signal from sensor circuit 114 causing solenoid actuator 204 to activate. Solenoid unit 160 acts as a pump, drawing air into plenum 202, and creating a vacuum in plenum 202. As the vacuum is created in plenum 202, exhaled air within air chamber 152 is drawn into and through fuel-cell sensor 158, as indicated by the arrow of FIG. 10.

Any alcohol that is present in the sampled air is absorbed by a working electrode of fuel-cell sensor 158, causing a spontaneous oxidation reaction of the alcohol at the electrode to take place. This results in the loss of electrons from the electrode's molecules. These electrons flow around an external circuit to a counter electrode, where oxygen from the air undergoes a concurrent reduction, thusly receiving the electrons.

This transfer of electrons from the alcohol electrode to the oxygen electrode via an external circuit constitutes an electric current. The larger the number of alcohol molecules that were present in the sample—in other words, the greater its concentration—then the more electrons that are generated, and so the greater the electric current that flows.

So by measuring the electric current that flows from the alcohol electrode in the fuel cell, or by measuring a voltage corresponding to the electric current, the concentration of alcohol that must have been present in the sampled breath can be determined by sensor circuit 114 and its processor.

After determining the user's BAC per the above steps, the results are transmitted to computer 112, and are displayed via display 104. Also, fuel-cell sensor 158 is cleared as indicated at step 360, air chamber 152 is cleared as indicated at step 362, and IBAC tester 100 is ready for another BAC test, as indicated at step 364.

With respect to the clearing of fuel-cell sensor 158, as described above, all alcohol contacting the electrode of fuel-cell sensor 158 is oxidized, creating an electrical current. The peak electrical current is used to determine actual BAC of the user. After the peak electrical current occurs, the oxidation process continues, as the remnant alcohol on the electrode dissipates, and as indicated by a decay of the rate of release of electrons. When the rate of release of electrons is close to zero, a BAC measurement is determined to be zero. This is the point at which fuel-cell sensor 158 is ready for another test.

The time that it takes for fuel-cell sensor 158 to be ready for a subsequent test depends largely on the amount of alcohol present in the sampled air. For example, it will take more time for fuel-cell sensor 158 to be ready for a subsequent test when the previously sampled exhaled air had a high alcohol content; it will take relatively less time for fuel-cell sensor 158 to be ready for a subsequent test when the previously-sampled exhaled air had a low alcohol content. In an embodiment, the time that must pass for fuel-cell sensor 158 to be ready for a subsequent test (fuel-cell sensor "clearing time") ranges from 0 to 15 seconds. In another embodiment, the fuel-cell sensor clearing time ranges from 0 to 30 seconds.

Some known breathalyzer and fuel-cell sensor patents or technologies provide techniques for reducing the fuel-cell sensor clearing time through devices and methods that speed up the natural decay of the release of electrons of the fuel-cell sensor electrodes.

However, such known devices and techniques as applied to known BAC testers ignore the effect of residual alcohol left in the BAC air chamber, focusing solely on the fuel-cell sensor clearing time as an indicator of time between BAC tests. Even after a fuel-cell sensor indicates a zero reading, residual alcohol can be left in the BAC air chamber, and if BAC tests are administered sequentially, with little wait time between tests, the residual alcohol in the air chamber can affect the accuracy of the subsequent test. Clearing of the air chamber becomes especially important for BAC testers that get repeated use over relatively short intervals.

The BAC tester of the present invention, IBAC tester 100, avoids such inaccuracies by promptly clearing residual alcohol-laden air from air chamber 152 in a fast and efficient manner.

As indicated at step 362, after a user's BAC is determined, air chamber 152 is cleared. The steps for clearing air chamber 152 are depicted and described by the flowchart of FIG. 11 and the depictions of FIGS. 12 to 14.

Figure 11:
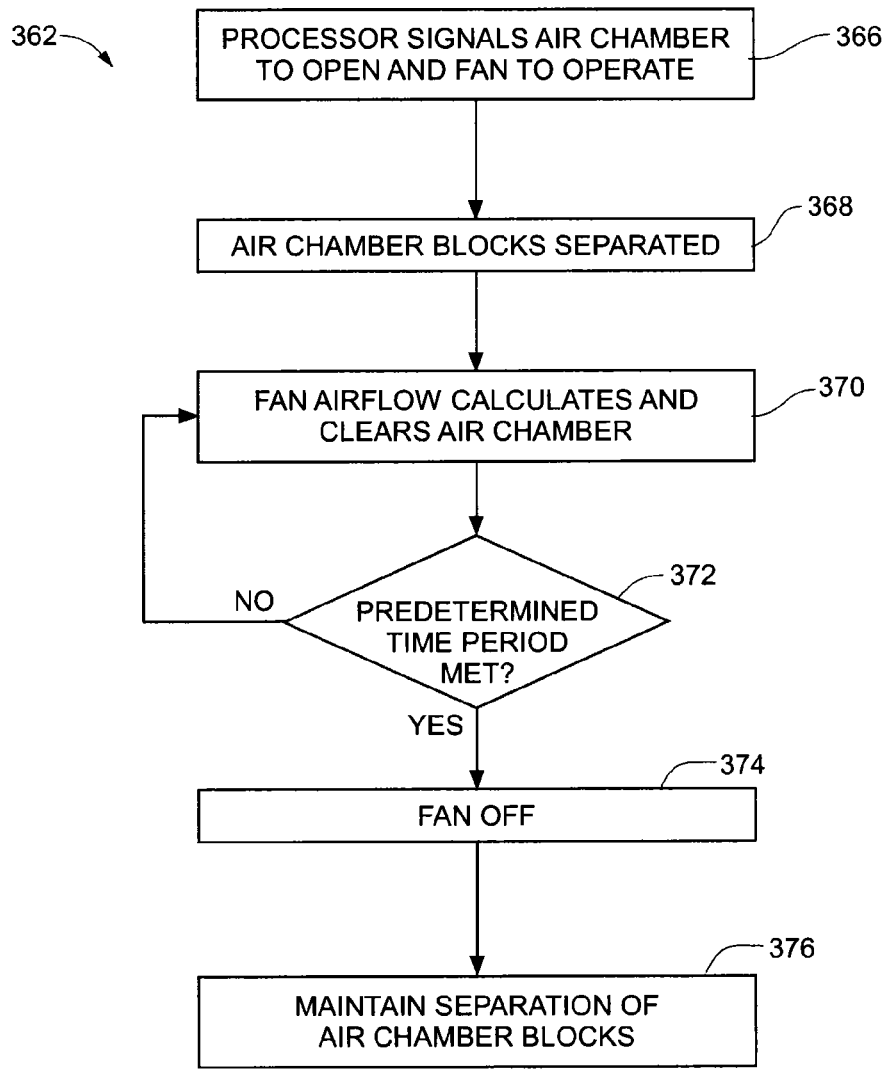
FIG. 11 is a flowchart depicting and describing the clearing of the air chamber step of the flowchart of FIG. 9.

Referring specifically to FIG. 11, at step 366, a processor of sensor circuit 114 signals air chamber 152 to be opened by having breath-sampling unit 128 separate second air-chamber block 172 from first air-chamber block 170.

At step 368, second air-chamber block 172 separates from first air-chamber block 170, thereby opening air chamber 152.

Figure 14:
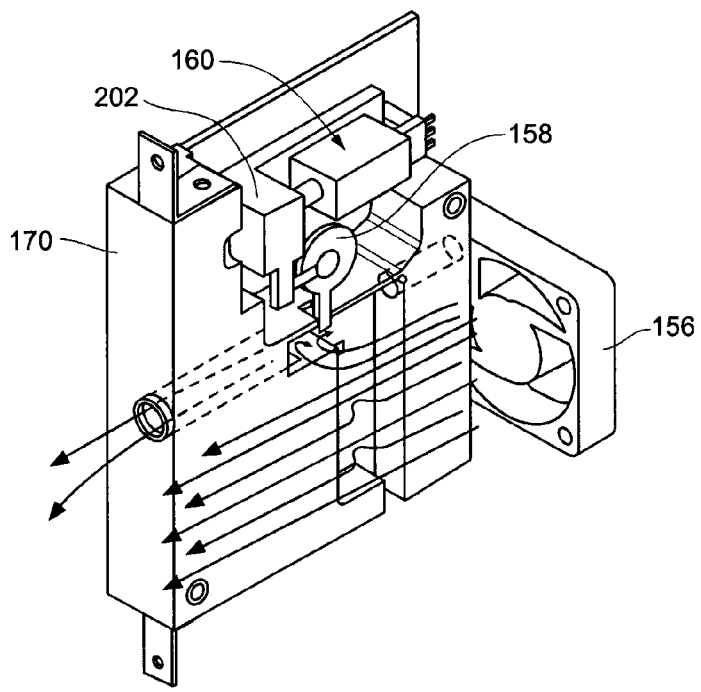
FIG. 14 is a front perspective view of the breath-sample capture portion of FIGS. 3a-3d, without the movable air-chamber block, and depicting purging air flow.
Figure 12:
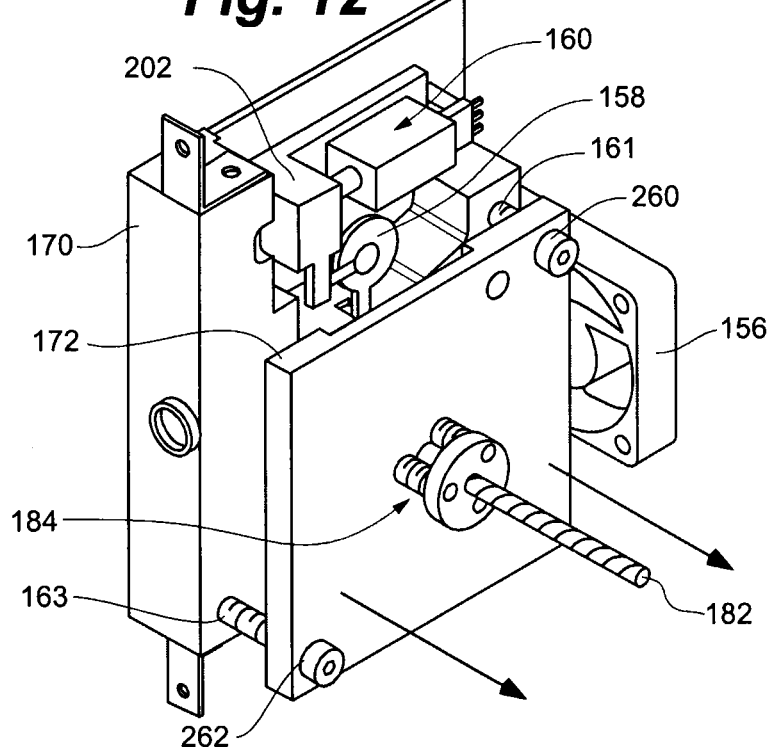
FIG. 12 is a front, left perspective view of the breath-sample capture portion of FIGS. 3a-3d, in an open position.
Figure 13:
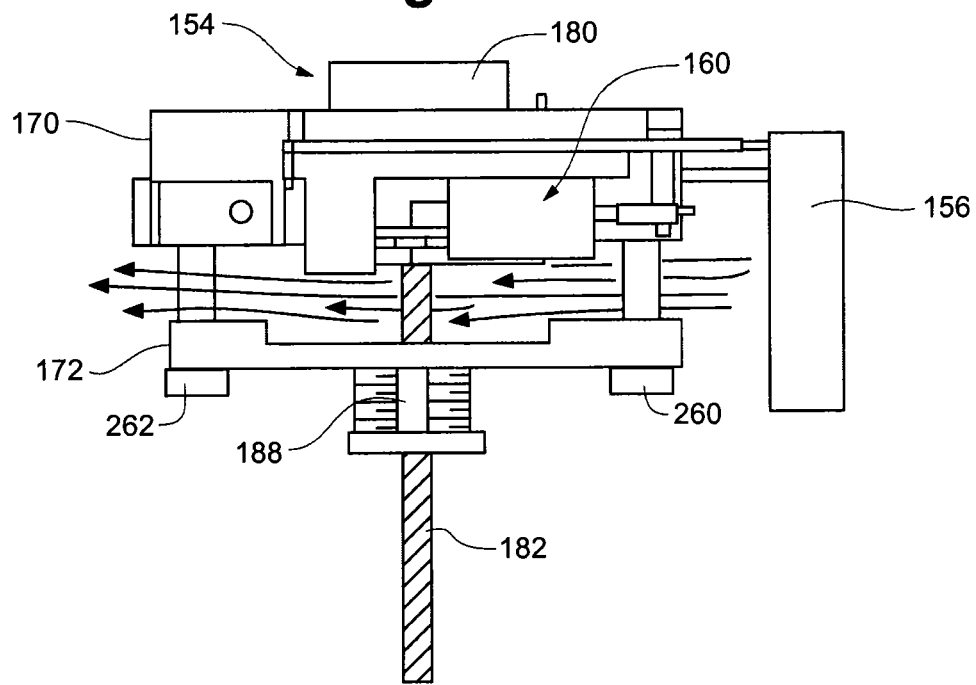
FIG. 13 is a top view of the breath-sample capture portion of FIGS. 3a-3d, in an open position, and depicting purging air flow.

Referring also to FIGS. 12 to 14, breath-sampling unit 128 in the open position is depicted.

FIG. 12 depicts a perspective view of second air-chamber block 172 separated from first air-chamber block 170, and FIG. 13 depicts a top view of second air-chamber block 172 separated from first air-chamber block 170.

During BAC testing, second air-chamber block 172 is adjacent first air-chamber block 170 (see FIGS. 3a to 3d). When BAC testing is completed, sensor circuit 114 causes drive unit 154 to drive second air-chamber block 172 outward and away from first air-chamber block 170.

More specifically, motor 180 receives an electrical signal from sensor circuit 114, causing the motor to turn, which causes threaded drive shaft 182 to rotate in a first direction. The rotation of drive shaft 182 through threaded block coupler 184, which is coupled to second air-chamber block 172, causes threaded block coupler 184 and attached second air-chamber block 172 to move outward and away from first air-chamber block 170 along guide posts 161 and 163, as depicted in FIG. 12, and as indicated by step 368 of FIG. 11. When outside surface 194 of second air-chamber block 172 is near or at flanges 260 and 262 of the guide posts, motor 180 stops driving second air-chamber block 172, and breath-sampling unit 128 and its air chamber 152 are in the open position.

In the meantime, sensor circuit 114 causes fan 156 to turn on and blow air (depicted by arrows) across the open breath-sampling unit 128 and open air chamber 152, as depicted in FIGS. 13 and 14. Air from fan 156 blows between first air-chamber block 170 and second air-chamber 172, and to a certain extent, around blocks 170 and 172. Air from fan 156 also enters air chamber 152. The air blown by fan 156 is air inside enclosure 102 that is drawn into enclosure 102 from the outside (also see FIGS. 1a and 1b). By blowing air into and around open air chamber 152, any residual air exhaled from users is exchanged for enclosure air blown by fan 156, and any built-up alcohol residue or moisture clinging to the surfaces of air chamber 152 is evaporated into the moving air.

In an embodiment, sensor circuit 114 controls fan 156, causing fan 156 to blow for a predetermined air-chamber clearing time. In one such embodiment, the predetermined air-chamber clearing time is a fixed time. In one such embodiment, the fixed time ranges from 15 to 30 seconds. In another embodiment, the fixed time ranges from one to two minutes.

In another embodiment, the predetermined air-chamber clearing time is dependent upon other variable factors, such as usage, or upon the fuel-cell sensor 158 clearing time. In one such embodiment, a minimum air-chamber clearing time is set equal to the fuel-cell sensor 158 clearing time; in another such embodiment, a look-up table of air-chamber clearing times vs. usage is stored in a database for reference and use. In such an embodiment, the more BAC tests conducted over a given period of time, the longer the air-chamber clearing time.

In an alternate embodiment, fan 156 continues to operate until a subsequent BAC test is initiated.

Referring still to FIG. 11, for the embodiment having a predetermined air-chamber clearing time, at step 372, if the predetermined air-chamber clearing time has not yet been met, fan 156 continues to operate. When the predetermined air-chamber clearing time has expired, at step 374, fan 156 is powered off.

At step 376, air-chamber blocks 170 and 172 are maintained in the open position until the next BAC test to allow enclosure air to be exposed to air chamber 152, rather than closing air chamber 152, thusly providing another opportunity for any residual alcohol in air chamber 152 to evaporate.

Referring again to FIG. 7b, after the BAC test is conducted, according to steps 380 and 382, if the user previously selected the guessing-game option or mode, the user's BAC is displayed on results display 106 as controlled by sensor circuit 114. Alternatively, the user's BAC may be displayed on primary display 104.

If the guessing game option was chosen, at step 384, the user's actual BAC test result is sent from sensor circuit 114 to computer 112, and both the user's BAC guess and BAC test result are displayed at primary display 104. The actual BAC test result may also be displayed on results display 106.

At step 386, the stored user BAC guess is compared to the BAC test result at computer 112, and if the user has correctly guessed his/her BAC, or if the user's guess is within a predetermined range of the actual BAC test result, then at step 388 a reward is provided.

Referring to FIG. 15, a flowchart depicting the details of step 388, providing an award, are described and depicted. IN the embodiment depicted, the reward is an activation code that enables the user to receive a free BAC test. However, it will be understood that IBAC tester 100 may provide other rewards, such as coupons, product or service discounts, some of which may be redeemable at the facility where the particular IBAC tester 100 is located.

At step 390, IBAC tester 100 determines that the user's BAC stored guess is correct, or is within range of the actual BAC test result.

At step 392, IBAC tester 100 indicates to the user that his/her guess was correct (essentially the same as step 384 of FIG. 7b).

At step 394, computer 112 generates, displays, and stores an activation code associated with that particular correct guess. Such an activation code is stored until the user activates and uses the code, or until a predetermined period of time passes.

In an embodiment, the reward or activation code may also be sent to a user, as indicated at steps 396 and 398. In one such embodiment, the activation code is texted via SMS texting, e-mailed, or otherwise transmitted to a device of a user. Referring also to FIG. 6, IBAC tester 100 may send an activation code to a user's mobile device 282.

To implement such a process, at step 396, IBAC tester 100 prompts a user to provide contact information, such as a mobile phone number, e-mail address, or similar. As part of this process, IBAC tester 100 may display a keypad on primary display 104 so that a user may enter his/her contact information into IBAC tester 100.

After receiving the user contact information at step 398, the activation code or other reward is transmitted to the user's device over the network depicted in FIG. 6, such as a WAN that includes the Internet, and possibly over another network in communication with the user's mobile device, as indicated at step 400. One such additional network includes a cellular telephone network. As such, a user conveniently receives an e-mail, text, or other such communication shortly after completing the BAC test.

During this time, ads may be displayed on primary display 104.

At step 402, an offer for transportation is made to the user. As described above, and as depicted in FIG. 8, an offer for transportation is also made prior to the BAC testing process. At the welcome screen, a user may depress a virtual button to summon transportation. The same offer for transportation may be made following BAC testing. In other embodiments, the offer for transportation is made available throughout all steps of the BAC testing process.

In an embodiment, at step 402, an offer to request a cab, limo, or other transportation is displayed to the user. If the offer is accepted, typically by having the user depress a virtual button displayed on primary display 104, at steps 404 and 406, transportation is requested. If the offer for transportation is declined, the BAC result and/or guess is removed from display at step 408, a "Thank You" screen is displayed at step 410, and the process reverts to displaying and cycling ads at step 300 of FIG. 7*a*.

Figure 16:
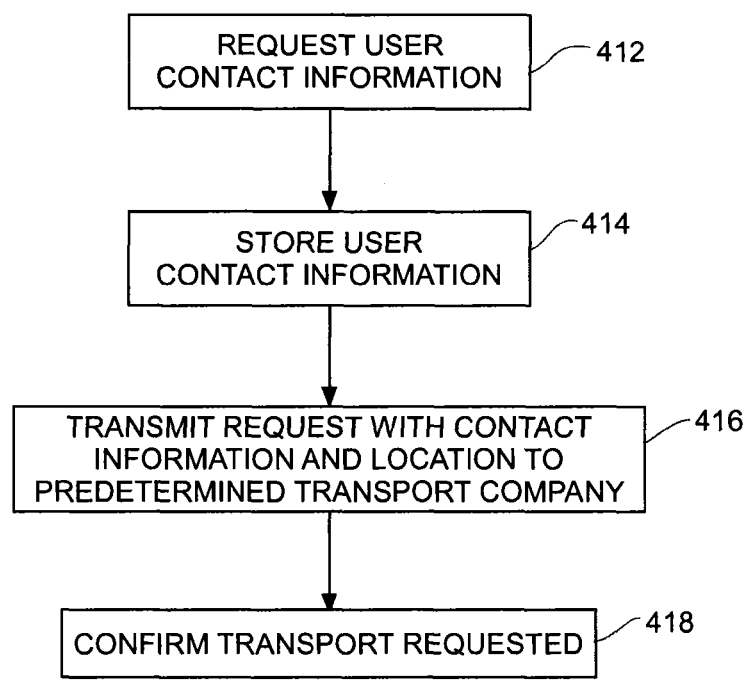
FIG. 16 is a flowchart depicting and describing the step of requesting transport of the flowchart of FIGS. 7a and 7b.

The details of step 406, an embodiment requesting transportation, are depicted and described in the flowchart of FIG. 16.

Prior to receiving a request for transportation, an IBAC tester 100 may be programmed with, or may be storing, contact information for a cab, taxi, limo, or other transport company. The contact information for the transportation company may include an e-mail address, or preferably, includes a phone number capable of receiving a text message. An operator may enter or change such information as needed by entering the transportation company's phone number in a cab call set-up menu of computer 112. A user may or may not be offered a choice as to which transportation company is summoned.

The location of the facility housing IBAC tester 100 is known, and may be stored in IBAC tester 100. The location may comprise GPS coordinates of the IBAC tester 100 or facility where the tester is located, or an address of the facility. In an embodiment, IBAC tester 100 includes a GPS device such that IBAC tester 100 may update its location information as needed. In other embodiments, stored location information may simply be updated, such as by remote-management system 270, in the event that the particular tester 100 is moved.

At step 412, contact information for the user is requested and received.

At step 414 the user contact information is stored in computer 112.

At step 416, IBAC tester 100 transmits a request for the transportation company to come to the location of the particular IBAC tester 100. Contact information for the user may also be transmitted to the transportation company so that the transportation company may contact the user as needed to confirm the transportation request at step 418. Such transmission is facilitated over the WAN depicted in FIG. 6

In a much simplified alternate embodiment, the user need only depress a virtual button, such as transportation request button 314 depicted in FIG. 8, and transportation will be requested per the steps described above, but without the need for the user to input contact information. Such an embodiment simplifies the transportation request process for those users who choose, or need, to simplify and expedite the process. In such an embodiment, computer 112 responds to transportation request button 314 being depressed by transmitting an SMS text message to a pre-selected transportation company, requesting that transportation be sent to the location of the particular IBAC tester 100.

Referring again to FIG. 2, after prolonged testing, it may be desirable to calibrate IBAC tester 100. In an embodiment, operator input 110 comprises a calibrate button. Such a calibrate button may be virtual, or may be physical button. By depressing the calibrate button, IBAC tester 100 enters the testing mode, as described above. Rather than performing an actual test, an operator may calibrate IBAC tester 100 and its fuel-cell sensor. Calibration may be accomplished by adjusting a scale on which the electrical output of the fuel-cell sensor 158 depends.

For example, after injecting ethanol-laden gas from a gas container having a known alcohol content into straw receiver 126, the operator observes the results as displayed on results display 106. If the results displayed do not match the known alcohol content of the gas, the operator may use up and down buttons of operator input 110 to adjust the displayed results reading to match the known alcohol content of the test gas.

In an embodiment, after adjustment, gas is again injected into air-chamber 152 through straw receiver 126. After a first predetermined period of time, which may be one second, the calibrate button may be depressed for a second predetermined period of time, which may be three seconds in an embodiment. Gas should be flowing throughout the two time periods, which in an embodiment is four seconds. After the predetermined period of time passes, IBAC tester 100 may provide an aural indication, such as a beep, to indicate that the calibration is complete. After this time, blocks 170 and 172 may separate, and the results of the calibration may be displayed on results display 106. The results may simply read "success" or "failure" depending on whether the calibration was successful. If not successful, another calibration attempt may be conducted by the operator.

As described above, the present invention therefore comprises devices, methods and systems for interactively, and accurately testing blood-alcohol content of a user. The advantages of the present invention over known BAC testers include the ability to quickly and efficiently clear the air chamber so as to minimize wait time between BAC tests and to improve overall BAC testing accuracy; the ability to provide detailed information and instructions to a user of the BAC tester through an interactive display, the ability to monitor, manage, and update the IBAC tester from remote locations over a network, thereby decreasing visits to the IBAC tester; a rewards system to encourage use of the IBAC tester; the ability to manage ads so as to create an ad-based revenue steam; and the ability to automatically request transportation directly, and simply, through the IBAC tester.

The embodiments of those above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An improved accuracy, rapidly-clearing blood-alcohol content (BAC) tester for use at a facility serving alcohol having high-volume usage with minimal wait-time between tests, the BAC tester comprising:
- a breath-sampling unit, the breath-sampling unit including:
  - an air-chamber unit defining a closed position and an open position, the air-chamber unit having:
    - a first air-chamber block comprising a generally planar surface and a cavity, and
    - a second air-chamber block comprising a generally flat plate,
    - the first air-chamber block and the second air-chamber block defining an air-chamber for receiving air exhaled from a user;
  - a drive unit operably coupled to the second air-chamber block;
  - an alcohol sensor for sensing the presence of alcohol in the air exhaled from the user; and
  - a fan configured to direct airflow to a vicinity of the air-chamber unit when the air-chamber unit is in the open position so as to remove residual air exhaled from the user, thereby rapidly clearing the air-chamber; and
- a sensor circuit communicatively coupled to the drive unit and the alcohol sensor;
- wherein the sensor circuit is configured to cause the drive unit to move the second-air chamber block relative to the first air-chamber block so as to cause the air-chamber unit to be in the closed or the open position
- wherein in the closed position, the generally flat plate of the second air-chamber block is adjacent to, and in contact with, the generally planar surface of the first air-chamber block and covers the cavity of the first air-chamber block thereby forming the air chamber.

2. The BAC tester of claim 1, wherein the sensor circuit is further configured to cause the drive unit to move the second-air chamber block in a direction transverse to the first air-chamber block so as to cause the air-chamber unit to be in the open position.

3. The BAC tester of claim 1, wherein the drive unit includes a motor and a threaded drive shaft, the drive shaft rotatably coupled to the motor and to a coupling unit attached to the second air-chamber block.

4. The BAC tester of claim 3, wherein the drive shaft projects perpendicularly to an inside, generally planar surface of the first air-chamber block, and the second air-chamber block is configured to move parallel to an axis of the drive shaft when the drive shaft is rotated.

5. The BAC tester of claim 1, further comprising a coupling unit attached to the second air-chamber block, the coupling unit including a central, threaded aperture engaging a threaded drive shaft of the drive unit.

* * * * *